United States Patent
Zhang et al.

(10) Patent No.: US 7,361,410 B2
(45) Date of Patent: Apr. 22, 2008

(54) EXTERNAL MODIFICATION OF COMPOSITE ORGANIC INORGANIC NANOCLUSTERS COMPRISING RAMAN ACTIVE ORGANIC COMPOUND

(75) Inventors: Jingwu Zhang, Santa Clara, CA (US); Xing Su, Cupertino, CA (US); Lei Sun, Santa Clara, CA (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 10/940,698

(22) Filed: Sep. 13, 2004

(65) Prior Publication Data

US 2006/0073336 A1    Apr. 6, 2006

Related U.S. Application Data

(63) Continuation-in-part of application No. 10/916,710, filed on Aug. 11, 2004, which is a continuation-in-part of application No. 10/830,422, filed on Apr. 21, 2004, now abandoned, which is a continuation-in-part of application No. 10/748,336, filed on Dec. 29, 2003, now abandoned.

(51) Int. Cl.
*B32B 5/16* (2006.01)
*B05D 3/02* (2006.01)

(52) U.S. Cl. .................. 428/551; 427/216; 427/220; 427/226; 428/407; 977/777; 977/783

(58) Field of Classification Search ............... 428/403, 428/407, 551, 570; 427/212, 216, 220, 226; 977/777, 783
See application file for complete search history.

(56) References Cited

U.S. PATENT DOCUMENTS

| 4,444,879 | A |   | 4/1984  | Foster et al. |
| 5,270,163 | A |   | 12/1993 | Gold et al. |
| 5,306,403 | A |   | 4/1994  | Vo-Dinh |
| 5,521,289 | A | * | 5/1996  | Hainfeld et al. ......... 530/391.5 |
| 5,567,588 | A |   | 10/1996 | Gold et al. |
| 5,670,637 | A |   | 9/1997  | Gold et al. |

(Continued)

FOREIGN PATENT DOCUMENTS

EP    0 587 008 A1    3/1994

(Continued)

OTHER PUBLICATIONS

Salata, "Applications of nanoparticles in biology and medicine", J. of Nanobiotechnology, 2004, 2.*

(Continued)

*Primary Examiner*—H. Thi Le
(74) *Attorney, Agent, or Firm*—Julia A. Hodge

(57) ABSTRACT

Modified and functionalized metallic nanoclusters capable of providing an enhanced Raman signal from an organic Raman-active molecule incorporated therein are provided. For example, modifications include coatings and layers, such as adsorption layers, metal coatings, silica coatings, and organic layers. The nanoclusters are generally referred to as COINs (composite organic inorganic nanoparticles) and are capable of acting as sensitive reporters for analyte detection. A metal that enhances the Raman signal from the organic Raman-active compound is inherent in the nanocluster. A variety of organic Raman-active compounds and mixtures of compounds can be incorporated into the nanocluster.

23 Claims, 17 Drawing Sheets

Gold Coated COINs

U.S. PATENT DOCUMENTS

| | | | |
|---|---|---|---|
| 5,696,249 | A | 12/1997 | Gold et al. |
| 5,712,105 | A | 1/1998 | Yanaihara et al. |
| 5,728,590 | A * | 3/1998 | Powell ........................ 436/547 |
| 5,766,963 | A | 6/1998 | Baldwin et al. |
| 5,843,653 | A | 12/1998 | Gold et al. |
| 6,002,471 | A | 12/1999 | Quake |
| 6,174,677 | B1 | 1/2001 | Vo-Dinh |
| 6,180,415 | B1 | 1/2001 | Schultz et al. |
| 6,219,137 | B1 | 4/2001 | Vo-Dinh |
| 6,263,286 | B1 | 7/2001 | Gilmanshin et al. |
| 6,514,767 | B1 * | 2/2003 | Natan ......................... 436/166 |
| 6,537,498 | B1 * | 3/2003 | Lewis et al. ............. 422/82.01 |
| 6,608,716 | B1 | 8/2003 | Armstrong et al. |
| 6,861,263 | B2 | 3/2005 | Natan |
| 6,989,897 | B2 * | 1/2006 | Chan et al. .................. 356/301 |
| 2002/0090662 | A1 | 7/2002 | Ralph |
| 2003/0211488 | A1 * | 11/2003 | Mirkin et al. .................. 435/6 |
| 2003/0232388 | A1 | 12/2003 | Kreimer et al. |
| 2005/0064435 | A1 | 3/2005 | Su et al. |
| 2005/0064604 | A1 | 3/2005 | Bohmann et al. |
| 2005/0089901 | A1 | 4/2005 | Porter et al. |
| 2005/0123974 | A1 | 6/2005 | Gilmanshin et al. |
| 2005/0130163 | A1 | 6/2005 | Smith et al. |
| 2005/0142567 | A1 * | 6/2005 | Su et al. ......................... 435/6 |
| 2005/0147963 | A1 * | 7/2005 | Su et al. ......................... 435/5 |
| 2005/0147976 | A1 | 7/2005 | Su |
| 2005/0147977 | A1 | 7/2005 | Koo et al. |
| 2005/0186576 | A1 | 8/2005 | Chan et al. |
| 2005/0191665 | A1 * | 9/2005 | Su et al. ......................... 435/6 |
| 2006/0033910 | A1 | 2/2006 | Sun et al. |
| 2006/0046311 | A1 | 3/2006 | Sun et al. |
| 2006/0046313 | A1 | 3/2006 | Roth et al. |
| 2006/0073336 | A1 | 4/2006 | Zhang et al. |
| 2006/0147941 | A1 | 7/2006 | Su |

FOREIGN PATENT DOCUMENTS

| | | |
|---|---|---|
| WO | WO 01/25758 A1 | 4/2001 |
| WO | WO 02/40698 A2 | 5/2002 |
| WO | WO 2005/062741 A2 | 7/2005 |
| WO | WO 2005/066370 A2 | 7/2005 |
| WO | WO 2005/066612 A2 | 7/2005 |
| WO | WO 2005/090948 A2 | 9/2005 |

OTHER PUBLICATIONS

"Strem Nanomaterials for Medical & Pharma Applications", Strem Chemicals brochure.*

Alivisatos, A.P., "Perspectives on the Physical Chemistry of Semiconductor Nanocrystals," J. Phys. Chem., vol. 100, 1996 (pp. 13226-13239).

Bosnick, et al., "Fluctuations and Local Symmetry in Single-Molecule Rhodamine 6G Raman Scattering on Silver Nanocrystal Aggregates," J. Phys. Chem. B., American Chemical Society, vol. 106, No. 33, 2002 (pp. 8096-8099).

Brody, et al., "Aptamers as therapeutic and diagnostic agents," Reviews in Molecular Biotechnology, vol. 74, 2000 (pp. 5-13).

Bruchez, "Qdot™ 655 Streptavidin Detection In Flow Cytometry," Quantum Dot Vision, Jun. 2003 (pp. 12-13).

Campion, et al., "Surface-Enhanced Raman Scattering," Chem. Soc. Rev., vol. 27, 1998 (pp. 241-250).

Cao, et al., "Nanoparticles with Raman Spectroscopic Fingerprints for DNA and RNA Detection," Science, vol. 297, Aug. 30, 2002 (pp. 1536-1540).

Craighead, "Nanoelectromechanical Systems," Science, vol. 290, 2000 (pp. 1532-1535).

De Bruin, et al., "Selection of High-Affinity Phage Antibodies from Phage Display Libraries," Nature Biotechnology, vol. 17, Apr. 1999 (pp. 397-399).

Doering, et al., "Spectroscopic Tags Using Dye-Embedded Nanoparticles and Surface-Enhanced Raman Scattering," Analytical Chemistry, American Chemical Society, vol. 75, No. 22, Nov. 15, 2003 (pp. 6171-6176).

Duffy, et al., "Rapid Prototyping of Microfluidic Systems in Poly(dimethylsiloxane)," Analytical Chemistry, vol. 70, No. 23, Dec. 1, 1998 (pp. 4974-4984).

Emory, et al., "Direct Observation of Size-Dependent Optical Enhancement in Single Metal Nanoparticles," J. Am. Chem Soc., vol. 120, No. 31, 1998 (pp. 8009-8010).

Fodor, et al., "Multiplexed Biochemical assays with Biological Chips," Nature, vol. 364, Aug. 5, 1993 (pp. 555-556).

Graham, et al., "Simple Multiplex Genotyping by Surface-Enhanced Resonance Raman Scattering," Analytical Chemistry, vol. 74, No. 5, Mar. 1, 2002 (pp. 1069-1074).

Grubisha, et al., "Femtomolar Detection of Prostate-Specific Antigen: An Immunoassay Based on Surface-Enhanced Raman Scattering and Immunogold Labels", Analytical Chemistry, American Chemical Society, Columbus, USA, vol. 75, No. 21, Nov. 1, 2003 (pp. 5936-5943), XP001047339, ISSN: 0003-2700.

Isola, et al., "Surface-Enhanced Raman Gene Probe for HIV Detection," Analytical Chemistry, American Chemical Society, vol. 70, No. 7, Apr. 1, 1998 (pp. 1352-1356).

Jain, "Nanotechnology in Clinical Laboratory Diagnostics", Clinica Chimica Acta, Amsterdam, NL, vol. 358, No. 1-2, Aug. 2005 (pp. 37-54), XP004976368, ISSN: 0009-8981.

Jaiswal, et al., "Long-Term Multiple Color Imaging of Live Cells Using Quantum Dot Bioconjugates," Nature Biotechnology, vol. 21, Jan. 2003 (pp. 47-51).

Jiang, et al., "Single Molecule Raman Spectroscopy at the Junctions of Large Ag Nanocrystals," J. Phys. Chem. B, American Chemical Society, vol. 107, No. 37, 2003 (pp. 9964-9972).

Kambhampati, et al., "on the Chemical Mechanism of Surface Enhanced Raman Scattering: Experiment and Theory," J. Chem, Phys., vol. 108, No. 12, Mar. 22, 1998 (pp. 5013-5023).

Kerker, M., "Electromagnetic Model for Surface-Enhanced Raman Scattering (SERS) on Metal Colloids," Acc. Chem. Res., vol. 17, 1984 (pp. 271-277).

Kneipp, et al., "Single Molecule Detection Using Surface-Enhanced Raman Scattering (SERS)," Physical Review Letters, vol. 78, No. 9, Mar. 3, 1997 (pp. 1667-1670).

Kneipp, et al., "Surface-Enhanced Raman Spectroscopy in Single Living Cells Using Gold Nanoparticles," Appl. Spectroscopy, vol. 56, No. 2, 2002 (pp. 150-154).

Kneipp, et al., "Ultrasensitive Chemical Analysis by Raman Spectroscopy," Chemical Reviews, American Chemical Society, 1999 (pp. 2957-2975).

MacBeath, et al., "Printing Proteins as Microarrays for High-Throughput Function Determination," Science, vol. 289, Sep. 8, 2000 (pp. 1760-1763).

Michaels, et al., "Ag Nanocrystal Junctions as the Site for Surface-Enhanced Raman Scattering of Single Rhodamine 6G Molecules," J. Phys. Chem. B, American Chemical Society, vol. 104, No. 50, 2000 (pp. 11965-11971).

Michaels, et al., "Surface Enhanced Raman Spectroscopy of Individual Rhodamine 6G Molecules on Large Ag Nanocrystals," J. Am. Chem. Soc., American Chemical Society, vol. 121, No. 43, 1999 (pp. 9932-9939).

Moore, et al., "Detection and Identification of *Mycobacterium tubeculosis* Directly from Sputum Sediments by Ligase Chain Reaction," Journal of Clinical Microbiology, vol. 36, No. 4, Apr. 1998 (pp. 1028-1031).

Mulvaney, et al., "Glass-Coated, Analyte-Tagged Nanoparticles: A New Tagging System Based on Detection with Surface-Enhanced Raman Scattering," Langmuir, American Chemical Society, Vo. 19, No. 11, 2003 (pp. 4784-4790).

Nam, et al., "Nanoparticle-Based Bio-Bar Codes for the Ultrasensitive Detection of Proteins," Science Magazine, vol. 301, Sep. 26, 2003 (pp. 1884-1886).

Ni, et al., "Immunoassay Readout Method Using Extrinsic Raman Labels Adsorbed on Immunogold Colloids," Analytical Chemistry, American Chemical Society, vol. 71, No. 21, Nov. 1, 1999 (pp. 4903-4908).

Nicewarner-Peña, et al., "Submicrometer Metallic Barcodes," Science, vol. 294, Oct. 5, 2001 (pp. 137-141).

Nie, et al., "Probing Single Molecules and Single Nanoparticles by Surface-Enhanced Raman Scattering," Science Magazine, vol. 275, Feb. 21, 1997 (pp. 1102-1106).

Otto, et al., "Surface Enhanced Raman Scattering," Journal of Physics: Condensed Matter, vol. 4, 1992 (pp. 1143-1212).

PCT International Search Report—dated Nov. 9, 2005, International Application No. PCT/US2004/043878—International Filing Date Dec. 28, 2004 (P18027X2PCT) (16 pages).

Sche, et al., "Display Cloning: Functional Identification of Natural Product Receptors Using cDNA-Phage Display," Chemistry & Biology, vol. 6, No. 10, 1999 (pp. 707-716).

Stadler, B.M., "Antibody Production Without Animals," Dev. Biol. Stand., vol. 101, 1999 (pp. 45-48).

Su, et al., "Composite Organic—Inorganic Nanoparticles (COINs) with Chemically Encoded Optical Signatures", Nano Letters, Jan. 2005, vol. 5, No. 1, (pp. 49-54), XP002350668, ISSN: 1530-6984.

U.S. Patent Appl. No. 11/081,772, Filed Mar. 15, 2005, entitled "Composite Organic Inorganic Nanoclusters", Inventors: Lei Sun, et al. (Ref. No. 42P20613).

U.S. Patent Appl. No. 11/216,112, Filed Sep. 1, 2005, entitled "Multiplex Data Collection and Analysis in Bioanalyte Detection", Inventors: Xing Su, et al. (Ref. No. 42P20614).

U.S. Pat. Appl. No. 11/325,833, Filed Dec. 30, 2005, entitled "Degenerate Binding Detection and Protein Identification Using Raman Spectroscopy Nanoparticle Labels", Inventors: Yamakawa, et al. (Ref. No. 42P20210).

Voldman, et al., "Microfabrication in Biology and Medicine," Annu. Rev. Biomed. Eng., vol. 1, 1999 (pp. 401-425).

Wittrup, K., "Phage on Display," Trends Biotechnol., vol. 17, 1999 (pp. 421-424).

Wu, et al., "Immunofluorescent labeling of cancer marker Her2 and other cellular targets with semiconductor quantum dots," Nature Biotechnology, Nature Publishing Group, vol. 21, Jan. 2003 (pp. 41-46).

Xu, et al., "Electromagnetic Contributions to Single-Molecule Sensitivity in Surface-Enhanced Raman Scattering," Physical Review E., vol. 62, No. 3, Sep. 2000 (pp. 4318-4324).

Xu, et al., "Multiplexed SNP genotyping using the Qbead™ system: a quantum dot-encoded microsphere-based assay," Nucleic Acids Research, vol. 31, No. 8 e43, 2003 (10 pages).

Xu, et al., "Spectroscopy of Single Hemoglobin Molecules by Surface Enhanced Raman Scattering," Physical Review of Letters, vol. 83, No. 21, Nov. 22, 1999 (pp. 4357-4360).

U.S. Pat. Appl. Ser. No. 11/527,895, Filed—Sep. 26, 2006, entitled Composite Organic Nanoclusters as Carriers and Identifiers of Tester Molecules, Inventor—Xing Su (Ref. No. 42P22333).

Han, et al., "Quantum-Dot-Tagged Microbeads for Multiplexed Optical Coding of Biomolecules", Nature Biotechnology, vol. 19, Jul. 2001 (pp. 631-635).

Non-Final Office Action (mailed Jul. 2, 2007), Appl. No. 11/026,857, Filing Date Dec. 30, 2004, First Named Inventor: Xing Su (30 pages).

Non-Final Office Action (mailed Jun. 29, 2007), Appl. No. 11/027,470, Filing Date Dec. 30, 2004, First Named Inventor: Mark Roth (25 pages).

Non-Final OA (mailed Apr. 9, 2007), Appl. No. 11/325,833, Filing Date Dec. 30, 2005, (16 pages).

PCT International Search Report (dated May 10, 2007), International Appl. No. PCT/US2005/031582—International Filing Date Sep. 2, 2005, (19 pages).

Non-Final Office Action (mailed Oct. 2, 2007), Appl. No. 11/021,682, Filing Date Dec. 23, 2004, First Named Inventor: Xing Su, 28 pages.

PCT Invitation to Pay Additional Fees (dated Feb. 7, 2007), International Application No. PCT/US2005/031582—International Filing Date Sep. 2, 2005, (6 pages).

* cited by examiner

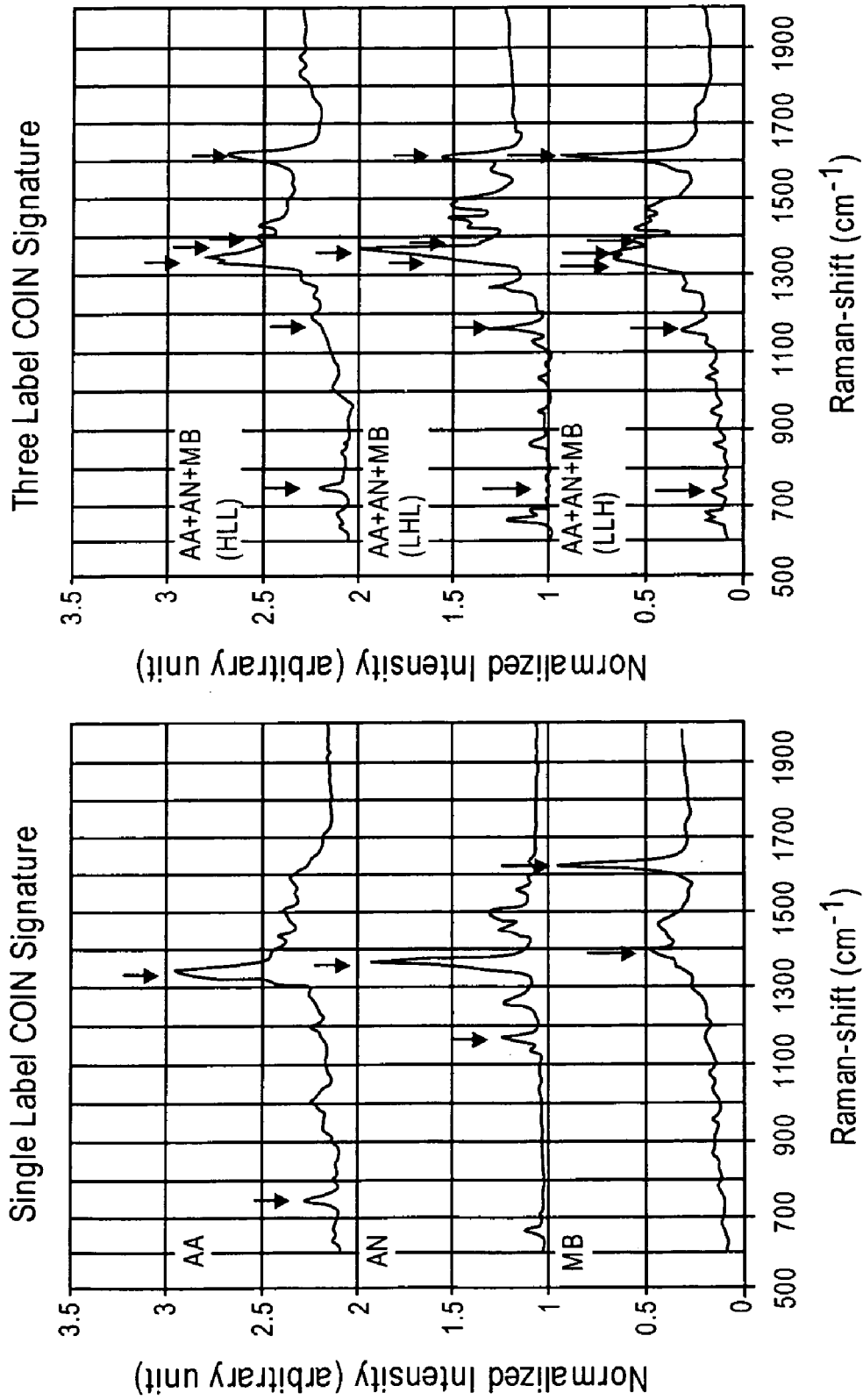

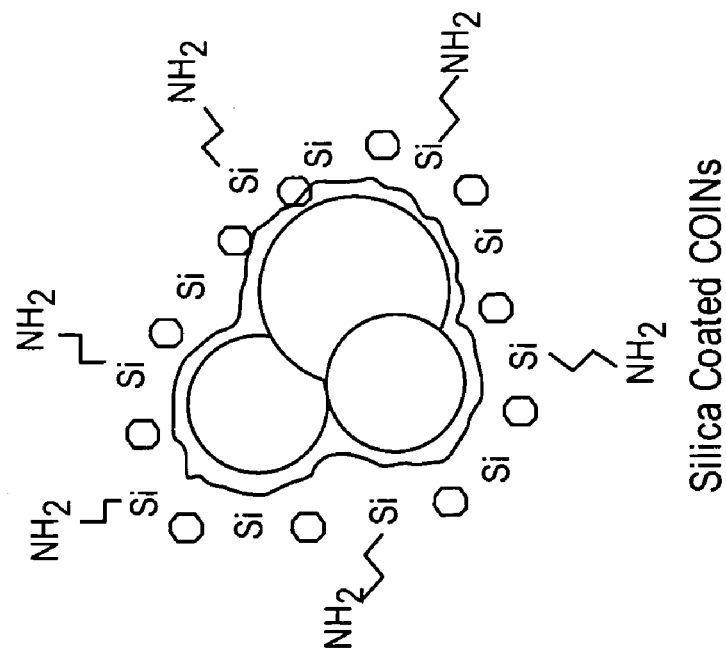
FIG. 6B Silica Coated COINs
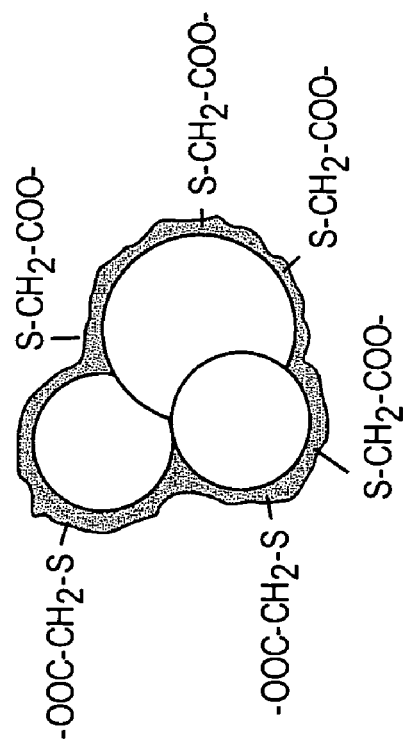
FIG. 6A Gold Coated COINs

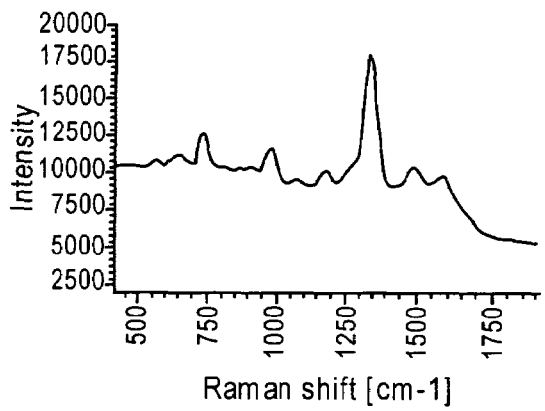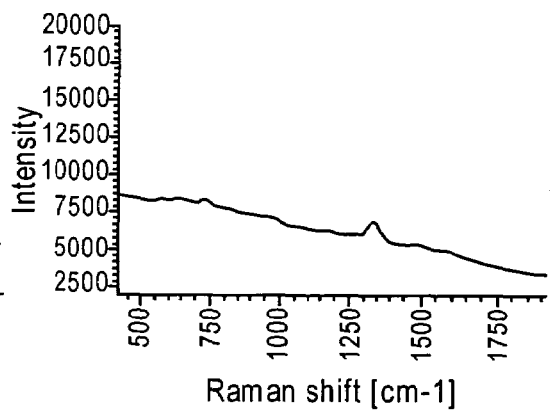
FIG. 12A  FIG. 12B
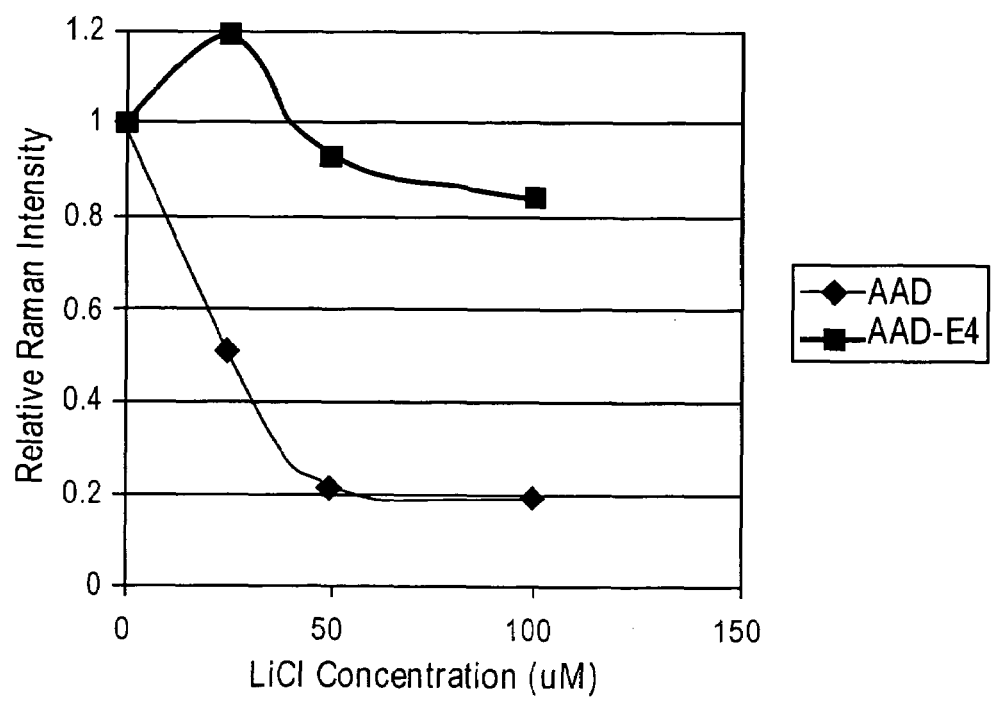
FIG. 12C

EXTERNAL MODIFICATION OF COMPOSITE ORGANIC INORGANIC NANOCLUSTERS COMPRISING RAMAN ACTIVE ORGANIC COMPOUND

The present invention is a continuation-in-part of U.S. patent application No. 10/916,710, filed Aug. 11, 2004, which is a continuation-in-part of U.S. patent application No. 10/830,422, filed Apr. 21, 2004 now abandoned, which is a continuation-in-part of U.S. patent application Ser. No. 10/748,336, filed Dec. 29, 2003 now abandoned, the disclosures of which are considered part of and are incorporated by reference in the disclosure of this application.

BACKGROUND OF THE INVENTION

1. Field of the Invention

The embodiments of the present invention relate generally to modification and functionalization of metallic nanoclusters that incorporate organic compounds.

2. Background Information

The ability to detect and identify trace quantities of analytes has become increasingly important in many scientific disciplines, ranging from part per billion analyses of pollutants in sub-surface water to analysis of treatment drugs and metabolites in blood serum. Additionally, the ability to perform assays in multiplex fashion greatly enhances the rate at which information can be acquired. Devices and methods that accelerate the processes of elucidating the causes of disease, creating predictive and/or diagnostic assays, and developing effective therapeutic treatments are valuable scientific tools. A principle challenge is to develop an identification system for a large probe set that has distinguishable components for each individual probe.

Among the many analytical techniques that can be used for chemical analyses, surface-enhanced Raman spectroscopy (SERS) has proven to be a sensitive method. A Raman spectrum, similar to an infrared spectrum, consists of a wavelength distribution of bands corresponding to molecular vibrations specific to the sample being analyzed (the analyte). Raman spectroscopy probes vibrational modes of a molecule and the resulting spectrum, similar to an infrared spectrum, is fingerprint-like in nature. As compared to the fluorescent spectrum of a molecule which normally has a single peak exhibiting a half peak width of tens of nanometers to hundreds of nanometers, a Raman spectrum has multiple structure-related peaks with half peak widths as small as a few nanometers.

To obtain a Raman spectrum, typically a beam from a light source, such as a laser, is focused on the sample generating inelastically scattered radiation which is optically collected and directed into a wavelength-dispersive spectrometer. Although Raman scattering is a relatively low probability event, SERS can be used to enhance signal intensity in the resulting vibrational spectrum. Enhancement techniques make it possible to obtain a $10^6$ to $10^{14}$ fold Raman signal enhancement.

A prerequisite for multiplex analyses in a complex sample is to have a coding system that possesses identifiers for a large number of analytes in the sample. Additionally, the identifiers, or reporters, for analyte detection may need to possess different properties depending on a user-selected application, such as for example, mechanical and/or chemical stability. Depending on the intended use, reporters may need to be chemically compatible with diverse applications, such as biochemical analyses and be capable of being stably functionalized over a variety of conditions with probes that allow for the complexation of the identifier with an analyte in a sample.

BRIEF DESCRIPTION OF THE FIGURES

The following drawings are included to further demonstrate certain aspects of the disclosed embodiments of the invention. The embodiments may be better understood by reference to one or more of these drawings in combination with the detailed description.

FIGS. 1A and B show Raman spectra obtained from COINs that incorporate a single type of Raman label and three different Raman labels, respectively. (Key: 8-azaadenine (AA), 9-aminoacridine (AN), methylene blue (MB).) Representative peaks are indicated by arrows; peak intensities have been normalized to respective maximums; the Y axis values are in arbitrary units; spectra are offset by 1 unit from each other.

FIG. 5A shows a nanocluster having a single protection layer. FIG. 5B shows a nanocluster having a double protection layer. FIG. 5C shows a nanocluster having a triple protection layer.

FIGS. 6A and B show examples of surface functionalized COINs. In FIG. 6A a COIN is coated with a layer of gold and functionalized with thiol alkyl acid. In FIG. 6B a COIN is coated with a silica layer and functionalized with ethylamine.

FIGS. 12A, B, and C show a thermostability study for encapsulated AAD COINs and BSA coated AAD COINs.

DETAILED DESCRIPTION OF THE INVENTION

As described more fully herein, composite organic inorganic nanoclusters (COINs) are composed of a metal and at least one organic Raman-active compound. Interactions between the metal of the clusters and the Raman-active compound(s) enhance the Raman signal obtained from the Raman-active compound(s) when the nanoparticle is excited by a laser. Thus, the COINs of the present invention can perform as sensitive reporters for use in analyte detection. Since a large variety of organic Raman-active compounds can be incorporated into the nanoclusters, a set of COINs can be created in which each member of the set has a Raman signature unique to the set. Thus, COINs can also function as sensitive reporters for highly parallel analyte detection. Furthermore, not only are the intrinsic enhanced Raman signatures of the nanoparticles of the present invention sensitive reporters, but sensitivity may also be further enhanced by incorporating thousands of Raman labels into a single nanocluster and/or attaching multiple nanoclusters to a single analyte.

It was found that aggregated metal colloids fused at elevated temperature and that organic Raman labels could be incorporated into the coalescing metal particles. These coalesced metal particles form stable clusters to produce intrinsically enhanced Raman scattering signals for the incorporated organic label. Thus, the COINs of the present invention do not require an amplification step to function as sensitive reporters for analyte detection since Raman enhancement is intrinsic in the particle. The interaction between the organic Raman label molecules and the metal colloids has mutual benefits. Besides serving as signal sources, the organic molecules induce a metal particle association that is in favor of electromagnetic signal enhancement. Additionally, the internal nanocluster structure provides spaces to hold Raman label molecules, especially in the junctions between the metal particles that make up the cluster. In fact, it is believed that the strongest enhancement is achieved from the organic molecules located in the junctions between the metal particles of the nanoclusters.

Figures 2A, 2B:
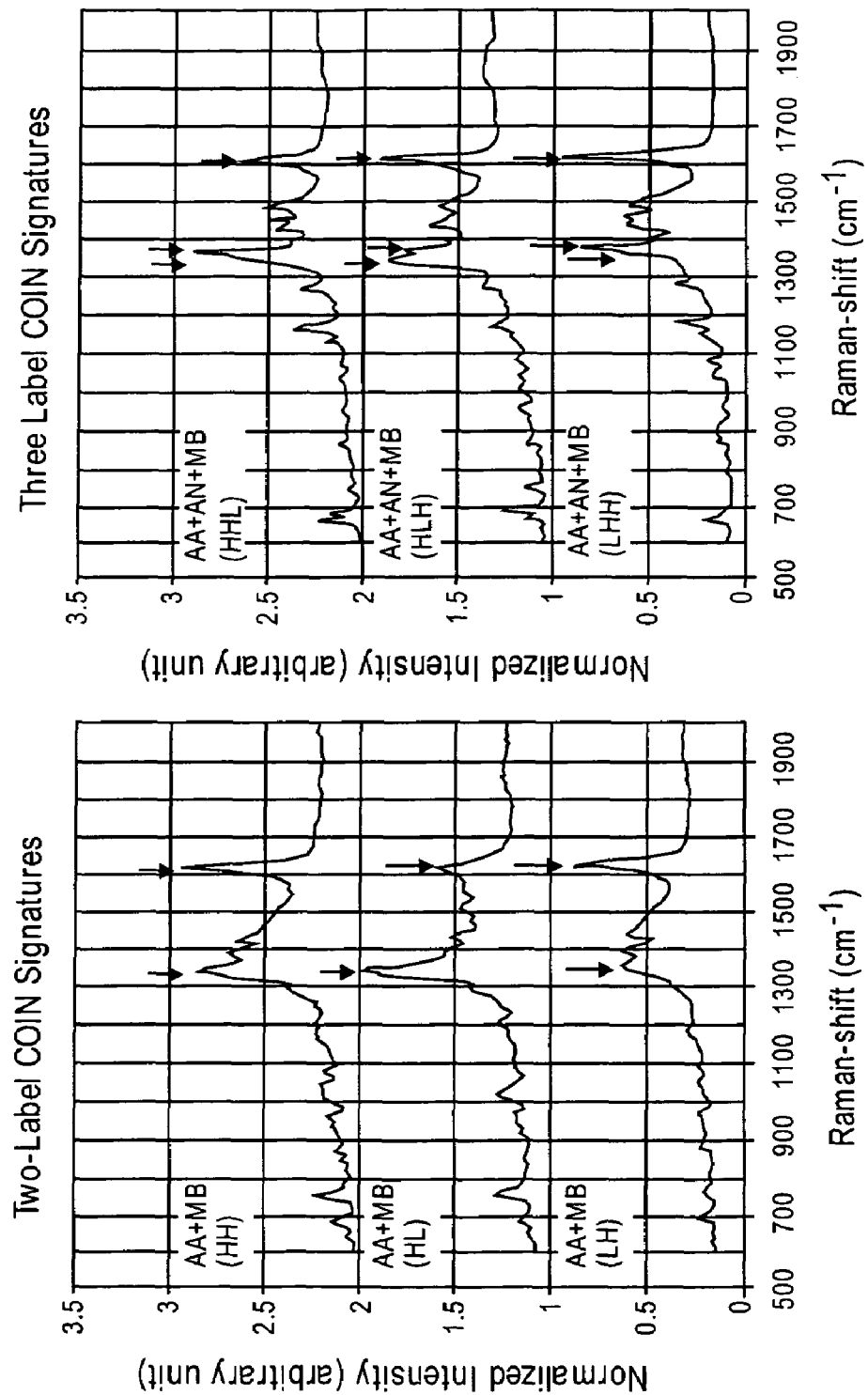
FIGS. 2A and B show signatures of COINs with double and triple Raman labels. The 3 Raman labels used were 8-aza-adenine (AA), 9-aminoacridine (AN), and methylene blue (MB). The main peak positions are indicated by arrows; the peak heights (in arbitrary units) were normalized to respective maximums; spectra are offset by 1 unit from each other.

Not only can COINS be synthesized with different Raman labels, but COINs may also be created having different mixtures of Raman labels and also different ratios of Raman labels within the mixtures. Referring now to FIGS. 1 and 2, FIG. 1A shows signatures of COINs made with a single Raman-active organic compound, demonstrating that each Raman-active organic compound produced a unique signature. FIG. 1B shows signatures of COINs made with mixtures of three Raman labels at concentrations that produced signatures as indicated: HLL means high peak intensity for 8-aza-adenine (AA) (H) and low peak intensity for both 9-aminoacridine (AN) (L) and methylene blue (MB) (L); LHL means low peak intensity for AA (L), high peak intensity for AN (H) and low for MB (L); LLH means low for both AA (L) and AN (L) and high for MB (H). COINs in these examples were made with individual or mixtures of Raman labels at concentrations from 2.5 µM to 20 µM, depending on the signature desired. Peak heights can be adjusted by varying label concentrations, but they might not be proportional to the concentrations of the labels used due to different absorption affinities of the Raman labels for the metal surfaces. FIG. 2A shows signatures of COINs made with 2 Raman labels (AA and MB) at concentrations designed to achieve the following relative peak heights: AA=MB (HH), AA>MA (HL), and AA<MB (LH). FIG. 2B shows Raman signatures of COINs made from mixtures of the 3 Raman labels at concentrations that produced the following signatures: HHL means high peak intensities for AA (H) and AN (H) and low peak intensity for MB (L); HLH means high peak intensity for AA (H), low peak intensity for AN (L), and high peak intensity for MB (H); and LLH means low peak intensities for AA (L) and AN (L), and high peak intensity for MB (H). COINs in these examples were made by the oven incubation procedure with mixtures of 2 or 3 Raman labels at concentrations from 2.5 to 20 µM, depending on the signatures desired. Thus, it is possible to create a large number of different molecular identifiers using the COINs of the present invention.

Using the OCAMF (organic compound assisted metal fusion)—based COIN synthesis chemistry, it is possible to generate a larger number of different COIN signatures by mixing a smaller number of Raman labels. Thus, COINs are especially suitable for use as identifiers in multiplexed assays. To demonstrate that multiple labels can be mixed to make COINs, we tested the combinations of 3 Raman labels for COIN synthesis. As shown in FIGS. 1 and 2, the results for one label, two labels, and three labels were all as expected. These spectral signatures demonstrated that closely positioned peaks (15 cm$^{-1}$ between AA and AN) could be resolved visually. In practical applications, mathematical and statistical methods can be used for signature reorganization. Theoretically, over a million COIN signatures could be made within the Raman shift range of 500-2000 cm$^{-1}$.

Table 1 provides examples of the types of organic compounds that can be used to build COINs. In general, Raman-active organic compound refers to an organic molecule that produces a unique SERS signature in response to excitation by a laser. In certain embodiments, Raman-active organic compounds are polycyclic aromatic or heteroaromatic compounds. Typically the Raman-active compound has a molecular weight less than about 500 Daltons. In addition, these compounds can include fluorescent compounds or non-fluorescent compounds. Exemplary Raman-active organic compounds include, but are not limited to, adenine, 4-amino-pyrazolo(3,4-d)pyrimidine, 2-fluoroadenine, N6-benzolyadenine, kinetin, dimethyl-allyl-amino-adenine, zeatin, bromo-adenine, 8-aza-adenine, 8-azaguanine, 6-mercaptopurine, 4-amino-6-mercaptopyrazolo(3,4-d)pyrimidine, 8-mercaptoadenine, 9-amino-acridine, and the like. Additional, non-limiting examples of Raman-active organic compounds include TRIT (tetramethyl rhodamine isothiol), NBD (7-nitrobenz-2-oxa-1,3-diazole), Texas Red dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, 5-carboxy-2',4',5',7'-tetrachlorofluorescein, 5-carboxyfluorescein, 5-carboxy rhodamine, 6-carboxyrhodamine, 6-carboxytetramethyl amino phthalocyanines, azomethines, cyanines, xanthines, succinylfluoresceins, aminoacridine, and the like. These and other Raman-active organic compounds may be obtained from commercial sources (such as, for example, Molecular Probes, Eugene, Oreg.). In certain embodiments, the Raman-active compound is adenine, 4-amino-pyrazolo(3,4-d)pyrimidine, or 2-fluoroadenine.

TABLE 1
| No. | Abbreviation | Name | Structure |
|---|---|---|---|
| 1 | AAD (AA) | 8-Aza-Adenine | 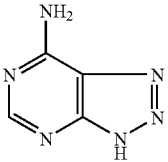 |
| 2 | BZA (BA) | N-Benzoyladenine | 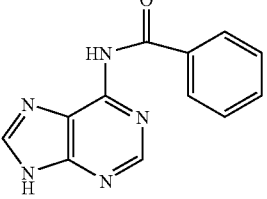 |
| 3 | MBI | 2-Mercapto-benzimidazole | 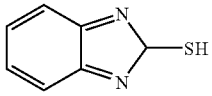 |
| 4 | APP | 4-Amino-pyrazolo[3,4-d]pyrimidine | 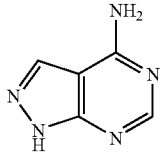 |
| 5 | ZEN | Zeatin | 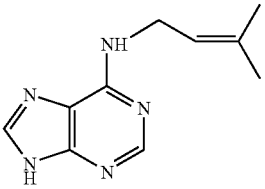 |
| 6 | MBL (MB) | Methylene Blue | 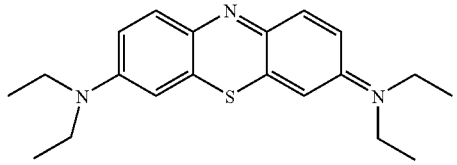 |
| 7 | AMA (AN, AM) | 9-Amino-acridine | 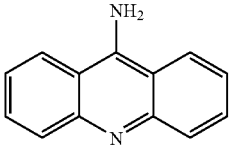 |
| 8 | EBR | Ethidium Bromide | 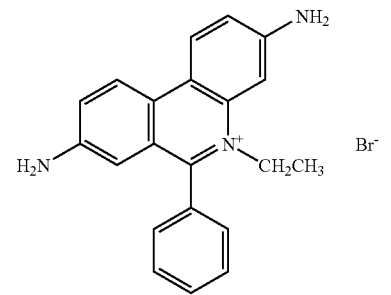 |

TABLE 1-continued

| No. | Abbreviation | Name | Structure |
|---|---|---|---|
| 9 | BMB | Bismarck Brown Y | 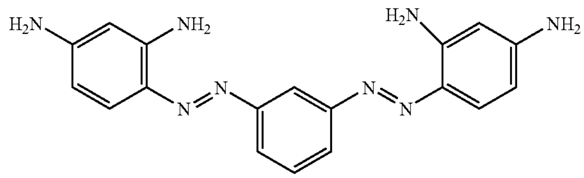 |
| 10 | NBA | N-Benzyl-aminopurine | 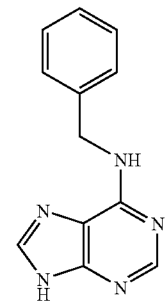 |
| 11 | THN | Thionin acetate | 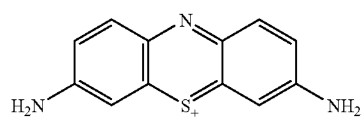 |
| 12 | DAH | 3,6-Diaminoacridine | 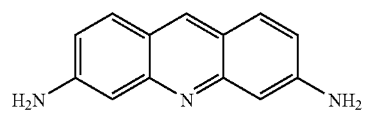 |
| 13 | CYP | 6-Cyanopurine | 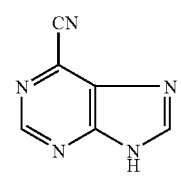 |
| 14 | AIC | 4-Amino-5-imidazole-carboxamide hydrochloride | 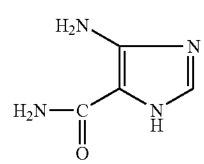 |
| 15 | DII | 1,3-Diiminoisoindoline | 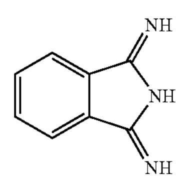 |
| 16 | R6G | Rhodamine 6G | 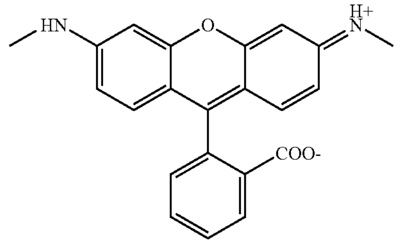 |

TABLE 1-continued
| No. | Abbreviation | Name | Structure |
|---|---|---|---|
| 17 | CRV | Crystal Violet | 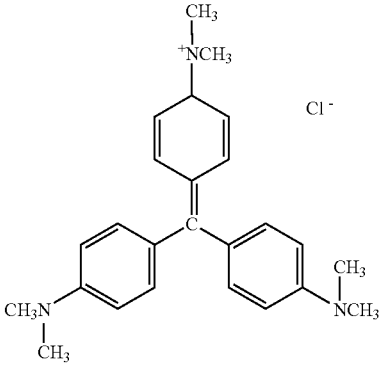 |
| 18 | BFU | Basic Fuchsin | 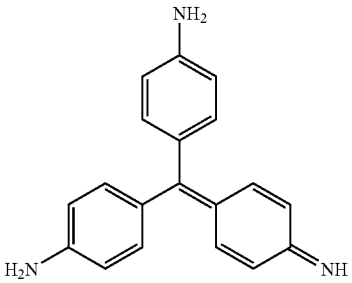 |
| 19 | ANB | Aniline Blue diammonium salt | 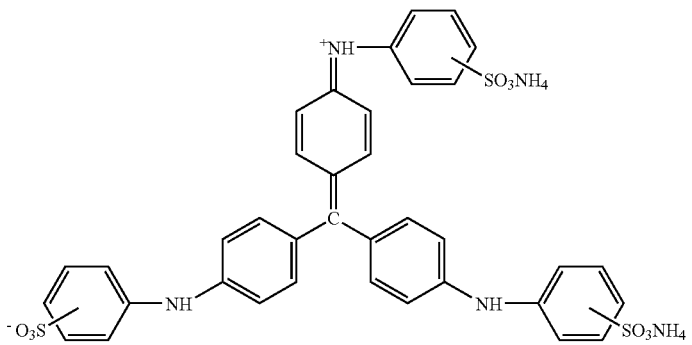 |
| 20 | ACA | N-[(3-(Anilinomethylene)-2-chloro-1-cyclohexen-1-yl)methylene]aniline monohydrochloride | 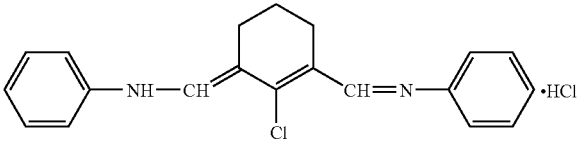 |
| 21 | ATT | O-(7-Azabenzotriazol-1-yl)-N,N,N',N'-tetramethyluronium hexafluorophosphate | 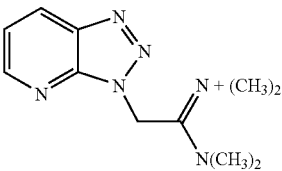 |
| 22 | AMF | 9-Aminofluorene hydrochloride | 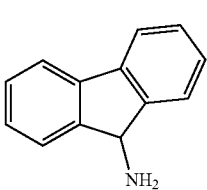 |

TABLE 1-continued

| No. | Abbreviation | Name | Structure |
|---|---|---|---|
| 23 | BBL | Basic Blue | 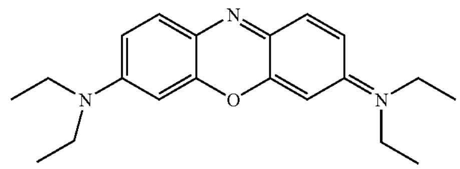 |
| 24 | DDA | 1,8-Diamino-4,5-dihydroxyanthraquinone | 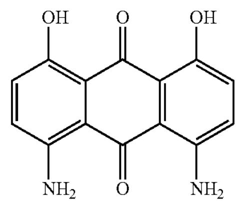 |
| 25 | PFV | Proflavine hemisulfate salt hydrate | 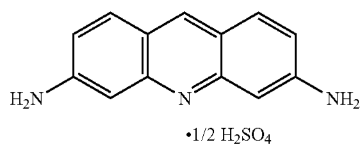 |
| 26 | APT | 2-Amino-1,1,3-propenetricarbonitrile | 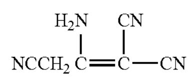 |
| 27 | VRA | Variamine Blue RT Salt | 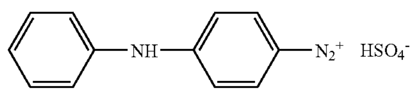 |
| 28 | TAP | 4,5,6-Triaminopyrimidine sulfate salt | 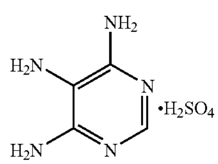 |
| 29 | ABZ | 2-Amino-benzothiazole | 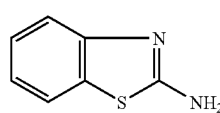 |
| 30 | MEL | Melamine | 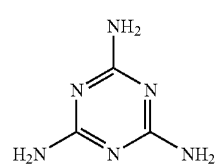 |
| 31 | PPN | 3-(3-Pyridylmethylamino)propionitrile | 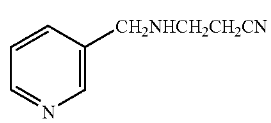 |
| 32 | SSD | Silver(I) sulfadiazine | 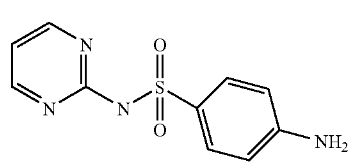 |

TABLE 1-continued

| No. | Abbreviation | Name | Structure |
|---|---|---|---|
| 33 | AFL | Acriflavine | |
| 34 | AMPT | 4-Amino6-Mercaptopyrazolo[3,4-d]pyrimidine | 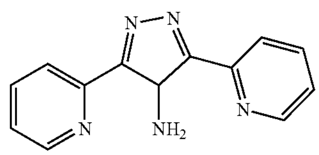 |
| 35 | APU | 2-Am-Purine | 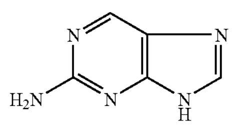 |
| 36 | ATH | Adenine Thiol | 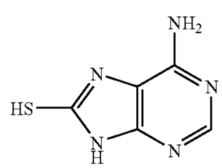 |
| 37 | FAD | F-Adenine | 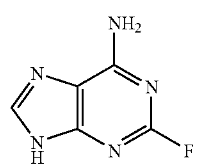 |
| 38 | MCP | 6-Mercaptopurine | 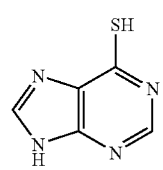 |
| 39 | AMP | 4-Amino-6-mercaptopyrazolo[3,4-d]pyrimidine | 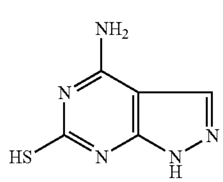 |
| 41 | R110 | Rhodamine 110 | 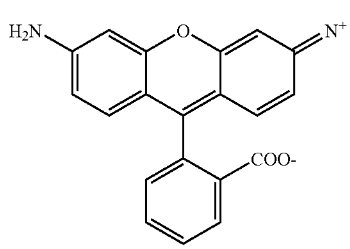 |

TABLE 1-continued

| No. | Abbreviation | Name |
|---|---|---|
| 42 | ADN | Adenine |
| 43 | AMB | 5-amino-2-mercaptobenzimidazole |

When fluorescent compounds are incorporated into nanoparticles described herein, the compounds include, but are not limited to, dyes, intrinsically fluorescent proteins, lanthanide phosphors, and the like. Dyes include, for example, rhodamine and derivatives, such as Texas Red, ROX (6carboxy-X-rhodamine), rhodamine-NHS, and TAMRA (5/6-carboxytetramethyl rhodamine NHS); fluorescein and derivatives, such as 5-bromomethyl fluorescein and FAM (5'-carboxyfluorescein NHS), Lucifer Yellow, IAEDANS, 7-Me$_2$, N-coumarin-4-acetate, 7-OH-4-CH$_3$-coumarin-3-acetate, 7-NH$_2$-4-CH$_3$-coumarin-3-acetate (AMCA), monobromobimane, pyrene trisulfonates, such as Cascade Blue, and monobromotrimethyl-ammoniobimane.

Figure 3:
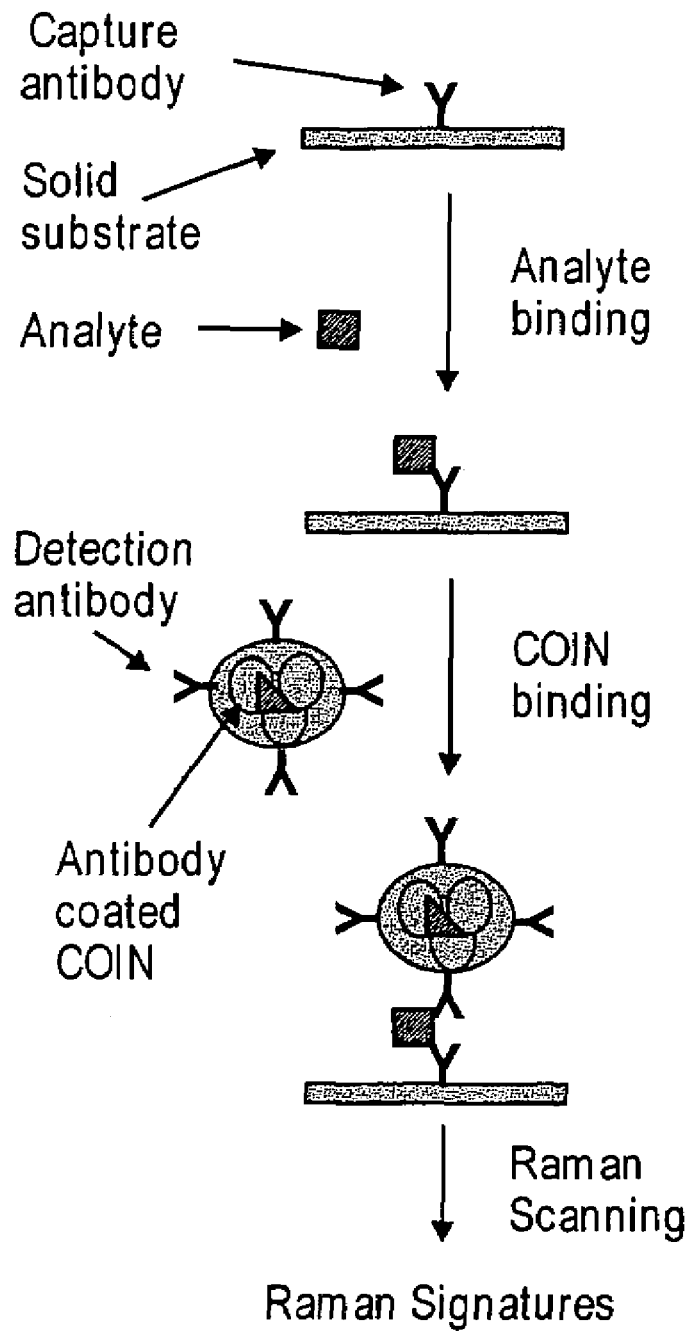
FIG. 3 is a schematic illustrating a use of COINs as reporters for analyte detection.

Referring now to FIG. 3, FIG. 3 diagrams a method that uses COINs as reporters for analyte detection. In this example a solution containing a known analyte is contacted with a substrate surface under conditions that allow the known analyte to be immobilized on the substrate surface through binding to a capture antibody specific for the analyte (an antibody that recognizes a first epitope of the analyte), attached to the substrate surface. A COIN having an attached probe specific for the analyte, in this case an antibody that recognizes a second epitope of the analyte, is then contacted with the substrate surface under conditions that allow the COIN-antibody conjugate to bind to the analyte. Unbound COINs are then washed from the substrate surface. The detection of the Raman signature of a COIN on the substrate surface indicates the presence of the analyte in the analysis sample. This analysis can also be performed in a multiplexed fashion. A set of COINs can be created having unique signatures and probes specific for two or more known analytes in a sample. In this case the detection of each unique COIN signal is indicative of the presence of a specific known analyte in the analysis sample.

The nanoparticles are readily prepared using standard metal colloid chemistry. Invention particles are less than 1 µm in size, and are formed by particle growth in the presence of organic compounds. The preparation of such nanoparticles also takes advantage of the ability of metals to adsorb organic compounds. Indeed, since Raman-active organic compounds are adsorbed onto the metal cluster during formation of the metallic colloids, many Raman-active organic compounds can be incorporated into a nanoparticle.

In general, COINs can be prepared by causing colloidal metallic nanoparticles to aggregate in the presence of an organic Raman label. The colloidal metal nanoparticles can vary in size, but are chosen to be smaller than the size of the desired resulting COINs. For some applications, for example, in the oven and reflux synthesis methods, silver particles ranging in average diameter from about 3 to about 12 nm were used to form silver COINs and gold nanoparticles ranging from about 13 to about 15 nm were used to make gold COINs. In another application, for example, silver particles having a broad size distribution of about 10 to about 80 nm were used in a cold synthesis method. Additionally, multi-metal nanoparticles may be used, such as, for example, silver nanoparticles having gold cores. To prepare the colloidal metal nanoparticles, an aqueous solution is prepared containing suitable metal cations and a reducing agent. The components of the solution are then subject to conditions that reduce the metallic cations to form neutral, colloidal metal particles. Since the formation of the metallic clusters occurs in the presence of a suitable Raman-active organic compound, the Raman-active organic compound is readily incorporated onto the metal nanocluster during colloid formation. It is believed that the organic compounds trapped in the junctions between the primary metal particles provide the strongest Raman signal. COINs are not usually spherical and often include grooves and protuberances and can typically be isolated by membrane filtration. In addition, COINs of different sizes can be enriched by centrifugation. Typical metals contemplated for use in formation of nanoparticles from metal colloids include, for example, silver, gold, copper, platinum, palladium, aluminum, gallium, indium, rhodium, and the like. In one embodiment the metal is silver or gold.

Figure 4:
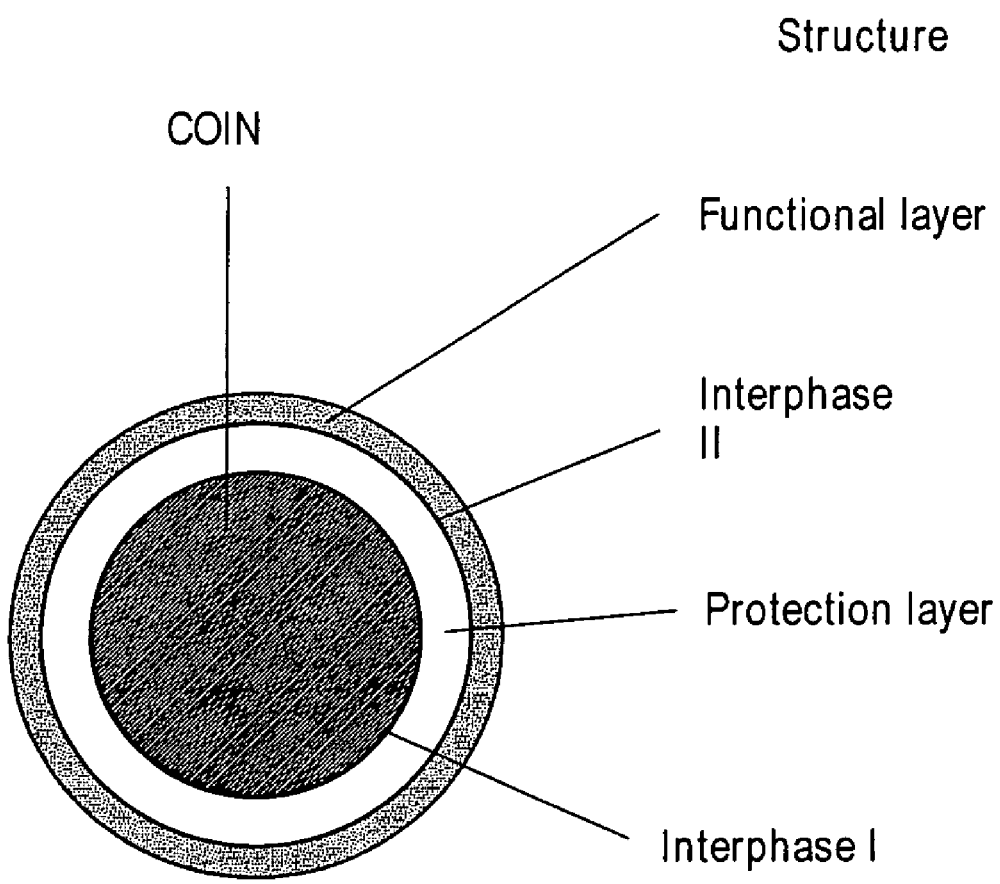
FIG. 4 provides an idealized schematic of a functionalized COIN.
Figure 5C:
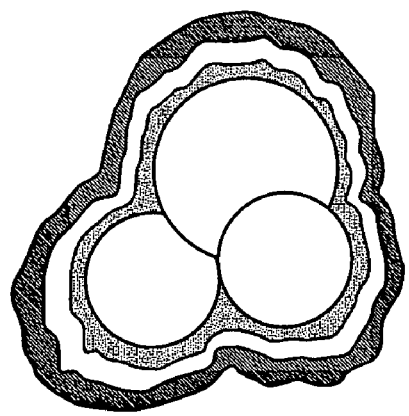
FIGS. 5A-C show diagrams of several coating schemes for COINs.
Figure 5B:
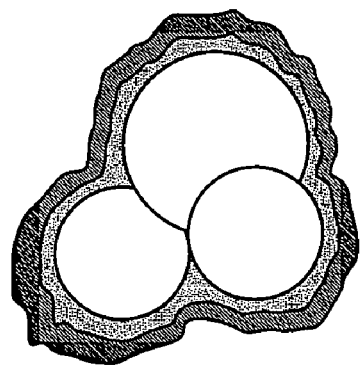
Figure 5A:
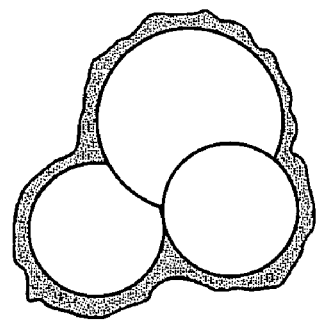

As can be seen in FIGS. 4 and 5, in general, COINs can be stabilized and/or functionalized with a number of different layers and combinations of layers. Referring to the generalized schematic in FIG. 4, the nanocluster is shown as a simplified darkened circle surrounded by a protection layer and a functional layer. Between the nanoparticle and the protection layer optionally is an interphase (Interphase I) consisting of a covalent or non-covalent linkage between the nanocluster and the protection layer. Optionally, a second interphase (Interphase II) exists between the protection layer and the functional layer consisting of a linkage between the protection layer and the functional layer (if the two layers are different). A functional layer can be a chemical derivatization layer containing sites for linker or probe attachment (probes such as biomolecules); the interphase II layer is an optional linkage between the derivatization layer and the protection layer (if they are different); the protection layer is a layer that provides chemical and/or physical stability; and the interphase I layer is a covalent or noncovalent linkage between the COIN and the protection layer. As can be seen from FIG. 5, different protection schemes, that is, different combinations of protection layers and/or functional layers, are used to give COINs enhanced chemical and colloidal stability and/or a surface that provides enhanced functionality for analytical applications.

In general, for applications using COINs as reporters for analyte detection, the average diameter of the resulting coated COIN particle should be less than about 200 nm. Typically, in analyte detection applications, COINs will range in average diameter from about 30 to about 200 nm. More preferably COINs range in average diameter from about 40 to about 200 mm, and more preferably from about 50 to about 200 mm, more preferably from about 50 to about 150 nm, and more preferably about 50 to about 100 nm. The thickness of the coating is in one aspect, limited by the weight of the resulting particle and its ability to remain suspended in solution. For example, coatings that are lighter, such as protein coatings, can be thicker than heavier silica and metal coatings. Typically, coatings that are less than about 100 nm thick yield COINs that can be suspended in solution. Depending on the application desired, coatings can be as thin as about one layer of molecules.

Typical coatings useful in embodiments of the present invention include coatings such as metal layers, adsorption layers, silica layers, hematite layers, organic layers, and organic thiol-containing layers. Typically, the metal layer is different from the metal used to form the COIN. Additionally, a metal layer can typically be placed underneath any of the other types of layers. Many of the layers, such as the adsorption layers and the organic layers provide additional mechanisms for probe attachment. For instance, layers presenting carboxylic acid functional groups allow the covalent coupling of a biological probe, such as an antibody, through an amine group on the antibody.

In an embodiment of the invention, the nanoclusters include a second metal different from the first metal, wherein the second metal forms a layer overlying the surface of the nanocluster. In certain embodiments, the metallic layer overlying the surface of the nanocluster is referred to as a protection layer. This protection layer contributes to aqueous stability of the colloidal nanoclusters. Metals that can be used include for example, silver, gold, platinum, aluminum, copper, zinc, iron, and the like. In one example, the COIN is comprised of silver and the coating metal is gold. Typically, metal-coated COINs range in average diameter from about 20 to about 200 nm, from about 30 to about 200 nm, from about 40 to about 200 nm, from about 50 to about 200 nm, or more preferably from about 50 to about 150 nm. Typically, the thickness of the layer will depend on variables, such as, the size of the nanoparticle to which the coating is applied, the thickness of other layers to be added, changes to the plasma resonance wavelength induced by the thickness of the coating, the ability of the particles to remain suspended in the solution.

To prepare nanoparticles coated with a second metal, COINs are placed in an aqueous solution containing a suitable second metal (as a cation) and a reducing agent. The components of the solution are then subject to conditions that reduce the second metallic cations, thereby forming a metallic layer overlying the surface of the nanoparticle. Metal-coated COINs can be isolated and/or enriched in the same manner as uncoated COINs.

In addition, COINs can be coated with a layer of gold by means of epitaxy growth. A procedure for growing gold particles developed by Zsigmondy and Thiessen (*Das Kolloide Gold* (Leipzig, 1925)), for example, may be employed. The growth medium contains chlorauric acid and hydroxylamine. The thickness of the gold coating can be controlled by the concentration of the COIN particles added to the growth medium.

It should be noted that the introduction of a gold layer is likely to change the plasma resonance wavelength. Thus, the thickness of the gold layer can be selected to tune the plasma resonance wavelength to more closely match the wavelength of the excitation source. For certain applications, the maximum thickness of the gold layer (or any other metal layer) is dictated by the resulting size of the COIN particle, such that if the particle becomes too heavy it will no longer remain suspended in solution.

Figure 7A:
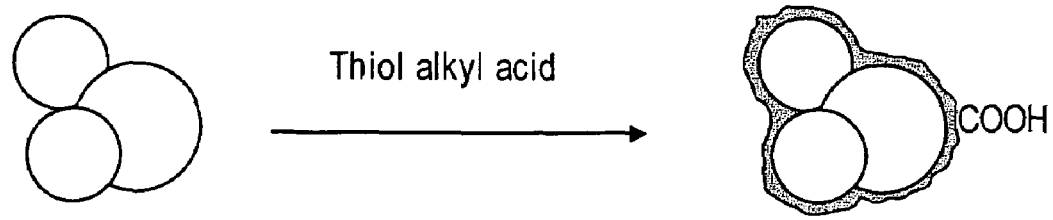
FIGS. 7A-D illustrate several methods for creating an adsorption layer on a COIN.

COINs and metal-coated COINs can be further functionalized through attachment of organic molecules to the surface. For example, gold and silver surfaces can be functionalized with a thiol-containing organic molecule to create an organic thiol layer. As shown in FIG. 6A, an organic molecule is attached through well-known gold-thiol chemistry. In the example in FIG. 6A, the organic molecule also contains a carboxyl group at the end distal from the thiol for further functionalization or derivatization, such as attachment of a linker molecule, coating, or probe. In FIG. 7A, sulfanyl acetic acid is adsorbed onto a COIN having a gold layer. The distal carboxylic acid group shown in FIG. 7A can be further functionalized, such as with an additional organic molecule, a peptide, a protein, a nucleic acid, or a probe. In certain embodiments, the organic thiol-containing molecule is a branched or straight-chain carbon-containing molecule having 2 to about 20 carbon atoms. In additional embodiments, the organic thiol-containing molecule is a polymer, such as for example a polyethylene glycol, a polysaccharide, a peptide containing cysteine, or a mixture thereof. In further embodiments, the organic thiol-containing molecule is capable of binding to a single COIN via two or more thiol groups. In several non-limiting examples, the thiol can be, 2,3-disulfanyl-1-propanol, 3,4-disulfanyl-1-butanol, 4,5-disulfanyl-1-pentanol, 4-amino-2-thiomethyl-butanethiol, or 5-amino-2-thiomethyl-hexanethiol. In general, useful thiol-containing organic molecules have a molecular weight of less than about 9,000. However, in the case of soluble polymers having thiol groups, such as polycysteine, peptides containing cysteine, peptides containing homocysteine, polysaccharides containing thiol groups, or polyethylene glycol polymers containing thiol group(s), the molecular weight can be about 10,000 or less. The organic thiol-containing molecule may also contain one or more additional functional groups, such as groups that allow for coupling with a probe. Useful additional functional groups include, for example, carboxyl groups, esters, amines, photolabile groups, and alcohols. Additionally, suitable functional groups include, but are not limited to, hydrazide, amide, chloromethyl, epoxy, tosyl, and the like, which can be coupled to molecules such as probes through reactions commonly used in the art. Photolabile groups, by which is meant a functional group that can be activated by applying electromagnetic radiation (usually near IR, ultraviolet, or visible light) at a specific wavelength, include, for example, the types of groups disclosed in Aslam, M. and Dent, A., *Bioconjugation: Protein Coupling Techniques for the Biomedical Sciences*, Grove's Dictionaries, Inc., 301-316 (1998). These functional groups may also be further modified after attachment to a COIN to form more reactive species for coupling, such as for example, oxidizing an alcohol to an aldehyde. Useful thiol-containing molecules include, for example, sulfanylacetic acid, 3-sulfanylpropanoic acid, 6-sulfanylhexanoic acid, 5-sulfanylhexanoic acid, 4-sulfanylhexanoic acid, 3-sulfanylpropylacetate, 3-sulfanyl-1,2-propanediol (1-thioglycerol), 4-sulfanyl-2-butanol, 3-sulfanyl-1-propanol (3-mercapto-1-propanol), ethyl-3-sulfanylpropanoate, cysteine, homocysteine, 2-aminoethanethiol, 4-aminobutanethiol, 4-amino-2-ethyl-butanethiol, and other similar organic molecules having a molecular weight of about 9,000 or less. Additionally, the organic thiol layer may be composed of mixtures of different organic thiol-containing molecules. The mixtures of organic thiol-containing molecules may include thiols having an additional functional group, such as one for probe attachment, and thiols not having an additional functional group, as well as mixtures of thiols containing different functional groups or comprised of different organic molecules. In a further embodiment, the thiol-containing organic layer is attached to a COIN comprised of gold or silver or a COIN having a gold or a silver metal layer. Synthesis of organic thiol layers can be accomplished by standard techniques, such as placing the COINs to be coated in an aqueous solution containing the organic thiol.

In further embodiments of the present invention, COINs are coated with an adsorption layer. The adsorption layer can be comprised of, for example, an organic molecule or a polymer, such as for example, a block co-polymer or a biopolymer, such as for example, a protein, peptide, or a polysaccharide. The adsorption layer, in some cases, stabilizes the COINs and facilitates the reduction or prevention of further aggregation and precipitation from solution. This layer also can provide bio-compatible functional surfaces for probe attachment and aid in the prevention of non-specific binding to the COIN.

COINs can be coated with an adsorption layer comprised of an amphiphilic block copolymer. In particular, block copolymers having a hydrophobic region and a hydrophilic region can be adsorbed to the surface of a COIN via hydrophobic interactions. The hydrophilic region of the block copolymer aids in the dispersal of the COIN in aqueous media and can provide a site for coupling additional molecules, layers, or probes. The individual blocks that form a polymer molecule can be identical (homopolymer) or can be different (heteropolymer). Hydrophilic heteropolymers may comprise, for example, some blocks that are charged (for example, anionic) and some blocks that are uncharged. At a minimum, the copolymer should contain two different types of blocks, such as for example, $A_xB_y$ or $A_xB_yA_z$ where A and B represent the different hetero- or homopolymer units (in the case of homopolymers, these units are monomers) of a block copolymer and X, Y, and Z are natural numbers (a diblock copolymer), however polymers having additional different blocks are also useful, such as for example, $A_xC_yB_z$, where A, B, and C represent different hetero- or homopolymer units (in the case of homopolymers these units are monomers) that make up a block copolymer and X, Y, and Z are natural numbers (a triblock copolymer). The number of repeating units that form each of the blocks of the block copolymer may the same or different. Additionally, the block copolymer may also contain functional groups for further modification or probe attachment. Typically, these functional groups will be located at or near the distal end of the hydrophilic section of the block copolymer for ease of further modification or probe attachment. Suitable functional groups include, but are not limited to carboxylic acid, esters, amines, hydroxyl, hydrazide, amide, chloromethyl, aldehyde, epoxy, tosyl, thiol, and the like, which can be coupled to molecules such as probes through reactions commonly used in the art. Further a coating may comprise a mixture of non-functionalized and functionalized copolymers, depending on the application and desire to adjust the number of probes or other molecules attached to a COIN surface. Ranges for mixtures of non-functionalized and functionalized block copolymers include, for example, about $10^6:1$ to about $1:10^6$ nonfunctionalized to functionalized block copolymer concentration. In general the block copolymer should have a molecular weight of about 1,000 to about 1,000,000, preferably about 1,000 to about 500,000, and more preferably about 1,000 to about 100,000. Suitable hydrophobic blocks include, but are not limited to, polyesters, polystyrenes, polyethylacrylate, polybutylacrylate, poly(propylene oxide), and poly(ethylene oxide). Suitable hydrophilic blocks include, but are not limited to, polyacrylamide/polyacrylic acid copolymers, poly(L-amino acid)s, poly(2-methacryloxyethyltrimethyl ammonium bromide), polystyrenesulfonic acid, and polystyrene-polystyrenesulfonic acid copolymers. For example the block copolymer can be a poly(L-amino acid)-block-polyester-block, polyglycol-block-poly(L-amino acid)-block, or a polystyrene-block-polystyrenesulfonic acid-block. Additional examples include, but are not limited to, polystyrene-block-poly(4-vinylpyridine)-block; polystyrene-block-poly(2-vinylpyridine)-block; polystyrene-block-poly(4-vinylphenol)-block; poly(4-vinylpyridine-block-poly(butyl methacrylate)-block; polystyrene-block-poly(maleic acid)-block; and poly(vinyl-1-chloride-co-vinyl acetate)-block-poly(maleic acid)-block. A block copolymer layer can be adsorbed on a COIN or a COIN coated with a metal layer, such as, for example, a silver COIN coated with a gold protection layer. A block copolymer adsorption layer can be prepared by dissolving the block copolymer in an aqueous solution containing the COINs and allowing the block copolymer to associate with the surface of the COINs.

Figure 7B:
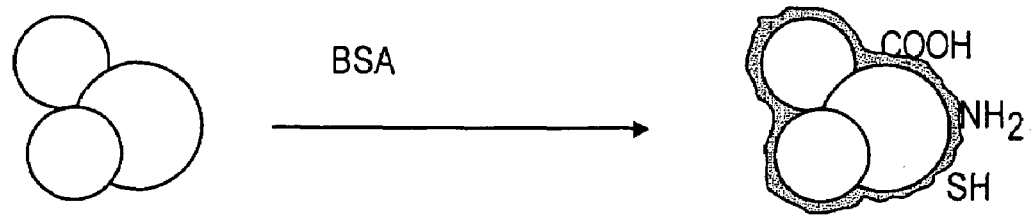

In a further embodiment, the COIN or the COIN having a metal layer is coated with an adsorbed layer of protein. Suitable proteins include non-enzymatic soluble globular or fibrous proteins. For applications involving molecular detection, the protein should be chosen so that it does not interfere with a detection assay, in other words, the proteins should not also function as competing or interfering probes in a user-defined assay. By non-enzymatic proteins is meant molecules that do not ordinarily function as biological catalysts. Examples of suitable proteins include avidin, streptavidin, bovine serum albumen (BSA), transferrin, insulin, soybean protein, casine, gelatine, and the like, and mixtures thereof. Referring now to FIG. 7B, for example, a layer of BSA, not only contributes to the stability of the COIN, but it also provides additional mechanisms for probe attachment. The bovine serum albumen layer affords several potential functional groups, such as, carboxylic acids, amines, and thiols, for further functionalization or probe attachment. Optionally, the protein layer can be cross-linked with EDC, or with glutaraldehyde followed by reduction with sodium borohydride.

Figure 7C:
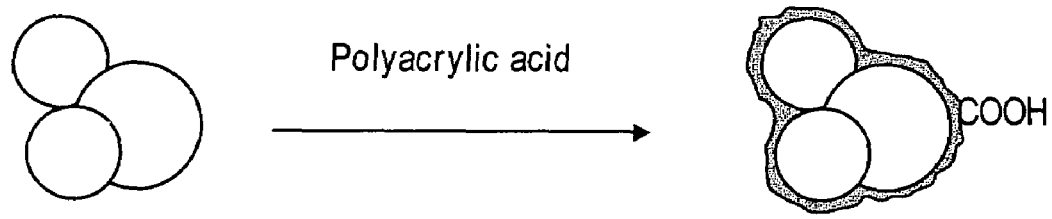
Figure 7D:
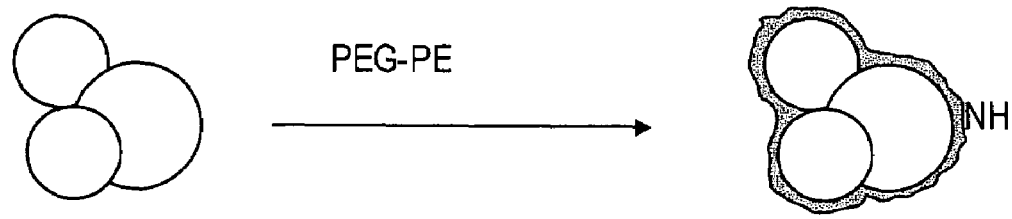

In additional embodiments a COIN or a metal-coated COIN is coated with a soluble polymeric adsorption layer. In general the soluble polymer should have a molecular weight of about 1,000 to about 1,000,000, preferably about 1,000 to about 500,000, and more preferably about 1,000 to about 100,000. For example, suitable polymeric adsorption layers include, polyacrylamide, partially hydrolyzed polyacrylamide, polyacrylic acid, polyacrylamide acrylic acid copolymers, polybutadiene-maleic acid copolymers, polyglycol-poly(L-amino acid) copolymers, polyethylenimine (branched or unbranched), PEG-PE (polyethylene glycol-phosphoethanolamine), poly(L-lysine hydrobromide), PGUA (polygalacturonic acid), or algenic acid. As shown in FIG. 7C, a polyacrylic acid layer is adsorbed onto a COIN and provides a carboxylic acid functional group for further derivatization or probe attachment though, for example, EDC coupling. FIG. 7D shows a PEG-PE layer adsorbed onto the COIN. A polymer adsorption layer can be prepared by dissolving the polymer in an aqueous solution containing COINs and allowing the polymer to associate with the surface of the COINs.

Figure 8:
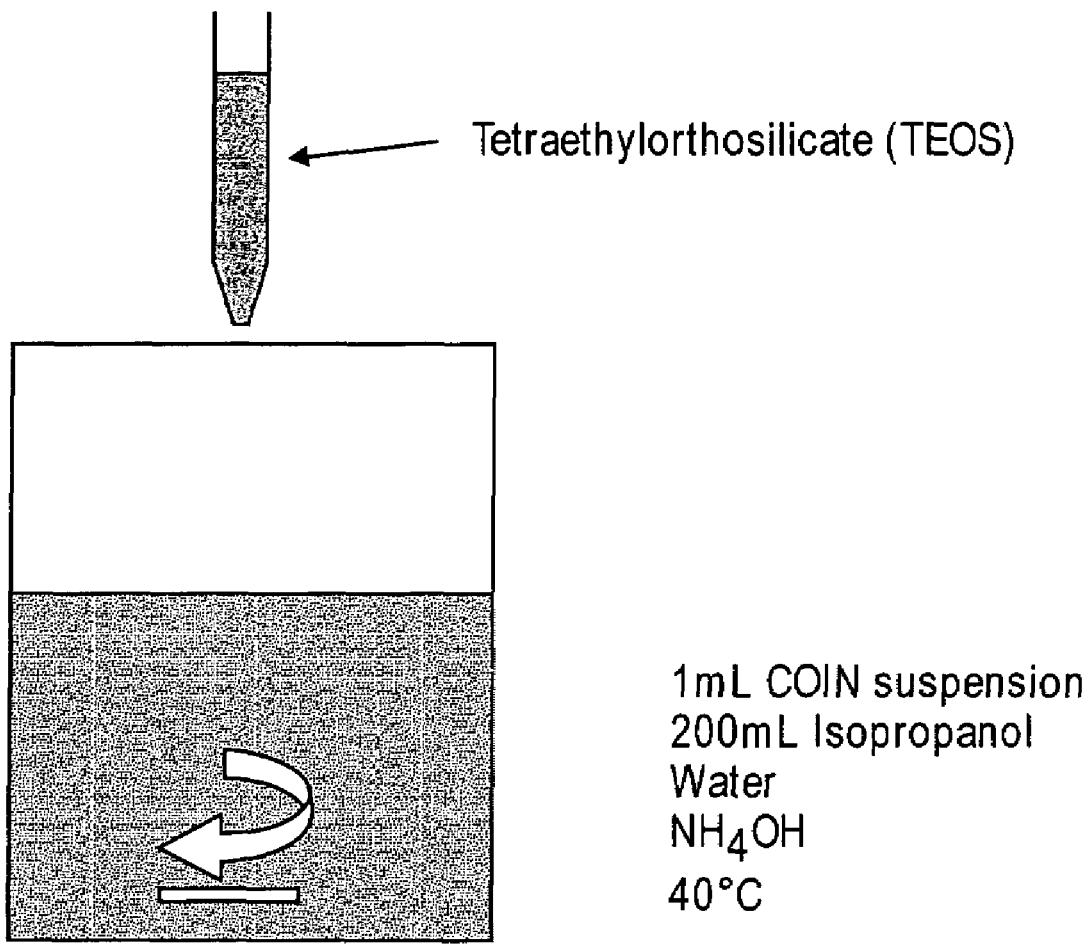
FIG. 8 is a schematic illustrating a method for coating silver COINs with silica.

As an alternative to metallic protection layers or in addition to metallic protection layers, COINs can be coated with a layer of silica. Silica deposition is initiated from a supersaturated silica solution, followed by growth of a silica layer through ammonia-catalyzed hydrolysis of tetraethyl orthosilicate (TEOS). Referring now to FIG. 6B, COINs can be coated with silica and functionalized, for example, with an organic amine-containing group. As shown in FIG. 8, a silver COIN or silver- or gold-coated COIN can be coated with a layer of silica via the procedure described in V. V. Hardikar and E. Matijevic, *J. Colloid Interface Science*, 221:133-136 (2000). Additionally, the silica-coated COINs are readily functionalized using standard silica chemistry. For example, a silica-coated COIN can be derivatized with (3-aminopropyl)triethoxysilane to yield a silica coated COIN that presents an amine group for further coating, layering, modification, or probe attachment. See, for example, Wong, C., Burgess, J., Ostafin, A., "Modifying the Surface Chemistry of Silica Nano-Shells for Immunoassays," *Journal of Young Investigators*, 6:1 (2002), and Ye, Z., Tan, M., Wang, G., Yuan, J., "Preparation, Characterization, and Time-Resolved Fluorometric Application of Silica-Coated Terbium(III) Fluorescent Nanoparticles," *Anal. Chem.*, 76:513 (2004). Additional layers or coatings that may be layered on a silica coating include the coatings and layers exemplified herein.

In alternative embodiments, COINs or metal-coated COINs can be coated with hematite ($Fe_2O_3$). The hematite coating can comprise a coating of iron oxide particles. Positively charged hematite particles will coat silver COINs, for example, through coulombic interactions. Hematite-coated COINs may be further functionalized with additional coatings. For example, coatings having carboxylic acid functional groups will tend to attach to the hematite particles. For example, a hematite-coated COIN may be further modified with a coating of polyacrylic acid, PGUA (polygalacturonic acid), or algenic acid.

Figure 9:
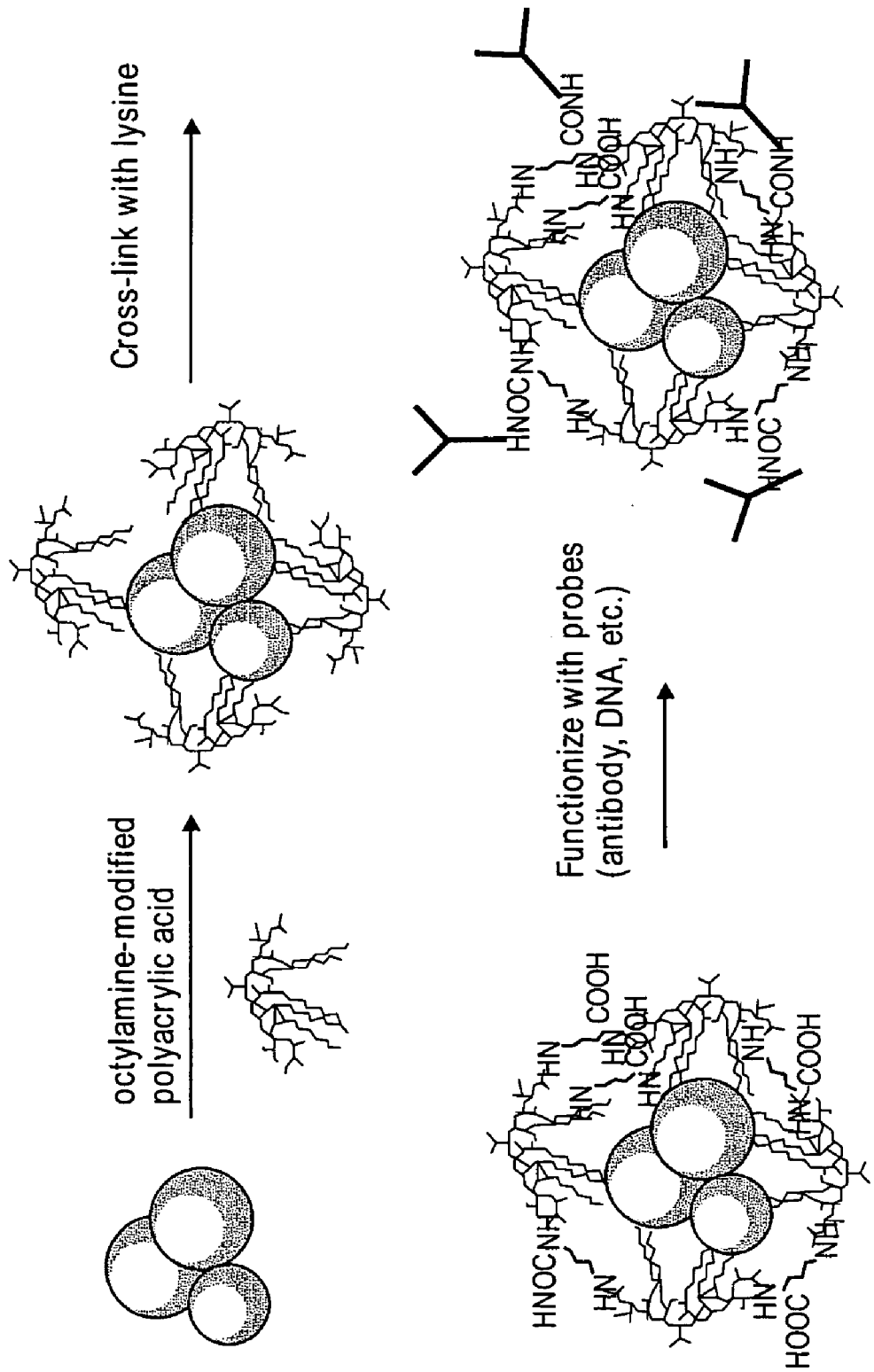
FIG. 9 illustrates a method for coating COINs with an organic material. An octylamine-modified polyacrylic acid is adsorbed to a nanocluster and crosslinked with lysine. A probe is then attached to the nanoparticle through coupling with the carboxylic acid group of the polyacrylic acid.

In other embodiments, COINs can include an organic layer. This organic layer can overlie another layer, such as a metal layer a silica layer, or a hematite layer. Typically, these types of nanocluster are prepared by covalently attaching organic compounds to the surface of the metal layer. Covalent attachment of an organic layer to the metallic layer can be achieved in a variety ways well known to those skilled in the art, such as for example, through thiol-metal bonds. An organic layer can also be used to provide colloidal stability and functional groups for further modification. The organic layer is optionally crosslinked to form a more unified coating. As shown in FIG. 9, an exemplary organic layer is produced by adsorption of an octylamine modified polyacrylic acid onto COINs, the adsorption being facilitated by the positively charged amine groups. The carboxyl groups of the polymer are then crosslinked with a suitable agent such as lysine, (1,6)-diaminoheptane, or the like. Unreacted carboxyl groups can be used for further derivation or probe attachment, such as through EDC coupling.

Further, the metal and organic coatings can be overlaid in various combinations to provide desired properties for the COINs. For example, silver COINs may be first coated with a gold layer to protect the more reactive silver before applying an adsorption layer, or silica or organic coating. Even if the outer layer is porous, the inner gold layer shields COINs from chemical attack by different compounds that may be present, for example, in a sample being assayed. Another example is to apply an adsorption layer on silica or gold layer to provide additional colloidal stability.

The COINs of the present invention can perform as sensitive reporters for use in fluid-based molecular analyte detection, and also for highly parallel analyte detection. A set of COINs can be created in which each member of the set has a Raman signature unique to the set. Any of the types of COINs as discussed above can be used for analyte detection. In general, COINs are composed of clusters of metal particles that contain Raman-active compounds. For example, COINs can range in average diameter from about 20 nm to about 200 nm. COINs can also be aggregated into larger clusters that range in average diameter from about 30 to about 200 nm, from about 40 to about 200 nm, or from 50 to about 150 nm.

COINs can be complexed to the molecular analyte through a probe attached to the COIN. An organic layer on the COIN is especially useful for covalent probe attachment. In general, a probe is a molecule that is able to specifically bind an analyte and, in certain embodiments, exemplary probes are antibodies, antigens, polynucleotides, oligonucleotides, carbohydrates, proteins, cofactors, receptors, ligands, peptides, inhibitors, activators, hormones, cytokines, and the like. For example, the analyte can be a protein and the COIN is complexed to the analyte through an antibody that specifically recognizes the protein analyte of interest.

In some embodiments, a probe is an antibody. As used herein, the term antibody is used in its broadest sense to include polyclonal and monoclonal antibodies, as well as antigen binding fragments of such antibodies. An antibody useful the present invention, or an antigen binding fragment thereof, is characterized, for example, by having specific binding activity for an epitope of an analyte. An antibody, for example, includes naturally occurring antibodies as well as non-naturally occurring antibodies, including, for example, single chain antibodies, chimeric, bifunctional, and humanized antibodies, as well as antigen-binding fragments thereof. Such non-naturally occurring antibodies can be constructed using solid phase peptide synthesis, can be produced recombinantly, or can be obtained, for example, by screening combinatorial libraries consisting of variable heavy chains and variable light chains. These and other methods of making, for example, chimeric, humanized, CDR-grafted, single chain, and bifunctional antibodies are well known to those skilled in the art.

The term binds specifically or specific binding activity, when used in reference to an antibody means that an interaction of the antibody and a particular epitope has a dissociation constant of at least about $1 \times 10^{-6}$, generally at least about $1 \times 10^{-7}$, usually at least about $1 \times 10^{-8}$, and particularly at least about $1 \times 10^{-9}$ or $1 \times 10^{-10}$ or less. As such, Fab, F(ab')$_2$, Fd and Fv fragments of an antibody that retain specific binding activity for an epitope of an antigen, are included within the definition of an antibody.

The term ligand implies a naturally occurring specific binding partner of a receptor, a synthetic specific-binding partner of a receptor, or an appropriate derivative of the natural or synthetic ligands. As one of skill in the art will recognize, a molecule (or macromolecular complex) can be both a receptor and a ligand. In general, the binding partner having a smaller molecular weight is referred to as the ligand and the binding partner having a greater molecular weight is referred to as a receptor.

By analyte is meant any molecule or compound. An analyte can be in the solid, liquid, gaseous or vapor phase. By gaseous or vapor phase analyte is meant a molecule or compound that is present, for example, in the headspace of a liquid, in ambient air, in a breath sample, in a gas, or as a contaminant in any of the foregoing. It will be recognized that the physical state of the gas or vapor phase can be changed for example, by pressure, temperature as well as by affecting surface tension of a liquid by the presence of or addition of salts.

The analyte can be comprised of a member of a specific binding pair (sbp) and may be a ligand, which is monovalent (monoepitopic) or polyvalent (polyepitopic), usually antigenic or haptenic, and is a single compound or plurality of compounds which share at least one common epitopic or determinant site. The analyte can be derived from a cell such as bacteria or a cell bearing a blood group antigen such as A, B, D, etc., or an HLA antigen or a microorganism, for example, bacterium, fungus, protozoan, prion, or virus. In certain aspects of the invention, the analyte is charged. A biological analyte could be, for example, a protein, a carbohydrate, or a nucleic acid.

A member of a specific binding pair (sbp member) is one of two different molecules, having an area on the surface or in a cavity which specifically binds to and is thereby defined as complementary with a particular spatial and polar organization of the other molecule. The members of the specific binding pair are referred to as ligand and receptor (antiligand) or analyte and probe. Therefore, a probe is a molecule that specifically binds an analyte. These will usually be members of an immunological pair such as antigen-antibody, although other specific binding pairs such as biotin-avidin, hormones-hormone receptors, IgG-protein A, polynucleotide pairs such as DNA-DNA, DNA-RNA, and the like are not immunological pairs but are included in the invention and the definition of sbp member.

Specific binding is the specific recognition of one of two different molecules for the other compared to substantially less recognition of other molecules. Generally, the molecules have areas on their surfaces or in cavities giving rise to specific recognition between the two molecules. Exemplary of specific binding are antibody-antigen interactions, enzyme-substrate interactions, polynucleotide hybridization interactions, and so forth. Non-specific binding is non-covalent binding between molecules that is relatively independent of specific surface structures. Non-specific binding may result from several factors including hydrophobic interactions between molecules.

In some embodiments, the organic layer can include a polynucleotide probe. A COIN-labeled oligonucleotide probe can be used in a hybridization reaction to detect a target polynucleotide. Polynucleotide is used broadly herein to mean a sequence of deoxyribonucleotides or ribonucleotides that are linked together by a phosphodiester bond. Generally, an oligonucleotide useful as a probe or primer that selectively hybridizes to a selected nucleotide sequence is at least about 10 nucleotides in length, usually at least about 15 nucleotides in length, for example between about 15 and about 50 nucleotides in length. Polynucleotide probes are particularly useful for detecting complementary polynucleotides in a biological sample and can also be used for DNA sequencing by pairing a known polynucleotide probe with a known Raman-active signal made up of a combination of Raman-active organic compounds as described herein.

A polynucleotide can be RNA or DNA, and can be a gene or a portion thereof, a cDNA, a synthetic polydeoxyribonucleic acid sequence, or the like, and can be single stranded or double stranded, as well as a DNA/RNA hybrid. In various embodiments, a polynucleotide, including an oligonucleotide (for example, a probe or a primer) can contain nucleoside or nucleotide analogs, or a backbone bond other than a phosphodiester bond. In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide or oligonucleotide also can contain nucleotide analogs, including non-naturally occurring synthetic nucleotides or modified naturally occurring nucleotides. One example of an oligomeric compound or an oligonucleotide mimetic that has been shown to have good hybridization properties is referred to as a peptide nucleic acid (PNA). In PNA compounds, the sugar-backbone of an oligonucleotide is replaced with an amide containing backbone, for example an aminoethylglycine backbone. In this example, the nucleobases are retained and bound directly or indirectly to an aza nitrogen atom of the amide portion of the backbone. PNA compounds are disclosed in Nielsen et al., *Science*, 254:1497-15 (1991), for example.

The covalent bond linking the nucleotides of a polynucleotide generally is a phosphodiester bond. However, the covalent bond also can be any of a number of other types of bonds, including a thiodiester bond, a phosphorothioate bond, a peptide-like amide bond or any other bond known to those in the art as useful for linking nucleotides to produce synthetic polynucleotides. The incorporation of non-naturally occurring nucleotide analogs or bonds linking the nucleotides or analogs can be particularly useful where the polynucleotide is to be exposed to an environment that can contain nucleolytic activity, including, for example, a tissue culture medium or upon administration to a living subject, since the modified polynucleotides can be less susceptible to degradation.

The nanoparticles of the present invention may be used to detect the presence of a particular target analyte, for example, a protein, enzyme, polynucleotide, carbohydrate, antibody, or antigen. The nanoparticles may also be used to screen bioactive agents, such as, drug candidates, for binding to a particular target or to detect agents like pollutants. As discussed above, any analyte for which a probe moiety, such as a peptide, protein, or aptamer, may be designed can be used in combination with the disclosed nanoparticles.

The polyvalent ligand analytes will normally be poly (amino acids), such as, polypeptides and proteins, polysaccharides, nucleic acids, and combinations thereof. Such combinations include components of bacteria, viruses, chromosomes, genes, mitochondria, nuclei, cell membranes and the like.

For the most part, the polyepitopic ligand analytes to which the subject invention can be applied will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

Molecular analytes include antibodies, antigens, polynucleotides, oligonucleotides, proteins, enzymes, polypeptides, polysaccharides, cofactors, receptors, ligands, and the like. The analyte may be a molecule found directly in a sample such as a body fluid from a host. The sample can be examined directly or may be pretreated to render the analyte more readily detectable. Furthermore, the analyte of interest may be determined by detecting an agent probative of the analyte of interest such as a specific binding pair member complementary to the analyte of interest, whose presence will be detected only when the analyte of interest is present in a sample. Thus, the agent probative of the analyte becomes the analyte that is detected in an assay. The body fluid can be, for example, urine, blood, plasma, serum, saliva, semen, stool, sputum, cerebral spinal fluid, tears, mucus, and the like. Methods for detecting target nucleic acids are useful for detection of infectious agents within a clinical sample, detection of an amplification product derived from genomic DNA or RNA or message RNA, or detection of a gene (cDNA) insert within a clone. Detection of the specific Raman label on the captured COIN labeled oligonucleotide probe identifies the nucleotide sequence of the oligonucleotide probe, which in turn provides information regarding the nucleotide sequence of the target polynucleotide.

In addition, the detection target can be any type of animal or plant cell, or unicellular organism. For example, an animal cell could be a mammalian cell such as an immune cell, a cancer cell, a cell bearing a blood group antigen such as A, B, D, etc., or an HLA antigen, or virus-infected cell. Further, the target cell could be a microorganism, for example, bacterium, algae, or protozoan. The molecule bound by the probe is present on the surface of the cell and the cell is detected by the presence of a known surface feature (analyte) through the complexation of a COIN to the target cell-surface feature. In general, cells can be analyzed for one or more surface features through the complexation of at least one uniquely labeled COIN to a known surface feature of a target cell. Additional surface features can be detected through the complexation of a differently labeled COIN to a second known surface feature of the target cell, or the complexation of two differently labeled COINs to a second and third surface feature, and so on. One or more cells can be analyzed for the presence of a surface feature through the complexation of a uniquely labeled COIN to a known surface feature of a target cell.

Cell surface targets include molecules that are found attached to or protruding from the surface of a cell, such as, proteins, including receptors, antibodies, and glycoproteins, lechtins, antigens, peptides, fatty acids, and carbohydrates. The cellular analyte may be found, for example, directly in a sample such as fluid from a target organism. The sample can be examined directly or may be pretreated to render the analyte more readily detectable. The fluid can be, for example, urine, blood, plasma, serum, saliva, semen, stool, sputum, cerebral spinal fluid, tears, mucus, and the like. The sample could also be, for example, tissue from a target organism.

In general, probes can be attached to metal-coated COINs through adsorption of the probe to the COIN surface. Alternatively, COINs may be coupled with probes through biotin-avidin coupling. For example, avidin or streptavidin (or an analog thereof) can be adsorbed to the surface of the COIN and a biotin-modified probe contacted with the avidin or streptavidin-modified surface forming a biotin-avidin (or biotin-streptavidin) linkage. As discussed above, optionally, avidin or streptavidin may be adsorbed in combination with another protein, such as BSA, and/or optionally crosslinked. In addition, for COINs having a functional layer that includes a carboxylic acid or amine functional group, probes having a corresponding amine or carboxylic acid functional group can be attached through water-soluble carbodiimide coupling reagents, such as EDC (1-ethyl-3-(3-dimethyl aminopropyl)carbodiimide), which couples carboxylic acid functional groups with amine groups. Further, functional layers and probes can be provided that possess reactive groups such as, esters, hydroxyl, hydrazide, amide, chloromethyl, aldehyde, epoxy, tosyl, thiol, and the like, which can be joined through the use of coupling reactions commonly used in the art. For example, Aslam, M and Dent, A, *Bioconjugation: Protein Coupling Techniques for the Biomedical Sciences*, Grove's Dictionaries, Inc., (1998) provides additional methods for coupling biomolecules, such as, for example, thiol maleimide coupling reactions, amine carboxylic acid coupling reactions, amine aldehyde coupling reactions, biotin avidin (and derivatives) coupling reactions, and coupling reactions involving amines and photoactivatable heterobifunctional reagents.

Nucleotides attached to a variety of tags may be commercially obtained (for example, from Molecular Probes, Eugene, Oreg.; Quiagen (Operon), Valencia, Calif.; and IDT (Integrated DNA Technologies), Coralville, Iowa) and incorporated into oligonucleotides or polynucleotides. Oligonucleotides may be prepared using commercially available oligonucleotide synthesizers (for example, Applied Biosystems, Foster City, Calif.). Additionally, modified nucleotides may be synthesized using known reactions, such as for example, those disclosed in, Nelson, P., Sherman-Gold, R., and Leon, R., "A New and Versatile Reagent for Incorporating Multiple Primary Aliphatic Amines into Synthetic Oligonucleotides," *Nucleic Acids Res.*, 17:7179-7186 (1989) and Connolly, B., Rider, P., "Chemical Synthesis of Oligonucleotides Containing a Free Sulfhydryl Group and Subsequent Attachment of Thiol Specific Probes," *Nucleic Acids Res.*, 13:4485-4502 (1985). Alternatively, nucleotide precursors may be purchased containing various reactive groups, such as biotin, hydroxyl, sulfhydryl, amino, or carboxyl groups. After oligonucleotide synthesis, COIN labels may be attached using standard chemistries. Oligonucleotides of any desired sequence, with or without reactive groups for COIN attachment, may also be purchased from a wide variety of sources (for example, Midland Certified Reagents, Midland, Tex.).

Probes, such as polysaccharides, may be attached to COINs, for example, through methods disclosed in Aslam, M. and Dent, A., *Bioconjugation: Protein Coupling Techniques for the Biomedical Sciences*, Grove's Dictionaries, Inc., 229, 254 (1998). Such methods include, but are not limited to, periodate oxidation coupling reactions and bis-succinimide ester coupling reactions.

Detection of Raman Signal

A variety of techniques can be used to analyze COINs. Such techniques include, for example, nuclear magnetic resonance spectroscopy (NMR), photon correlation spectroscopy (PCS), IR, surface plasma resonance (SPR), XPS, scanning probe microscopy (SPM), SEM, TEM, atomic absorption spectroscopy, elemental analysis, UV-vis, fluorescence spectroscopy, and the like.

In the practice of the present invention, the Raman spectrometer can be part of a detection unit designed to detect and quantify nanoparticles of the present invention by Raman spectroscopy. Methods for detection of Raman labeled analytes, for example nucleotides, using Raman spectroscopy are known in the art. (See, for example, U.S. Pat. Nos. 5,306,403; 6,002,471; 6,174,677). Variations on surface enhanced Raman spectroscopy (SERS), surface enhanced resonance Raman spectroscopy (SERRS) and coherent anti-Stokes Raman spectroscopy (CARS) have been disclosed.

A non-limiting example of a Raman detection unit is disclosed in U.S. Pat. No. 6,002,471. An excitation beam is generated by either a frequency doubled Nd:YAG laser at 532 nm wavelength or a frequency doubled Ti:sapphire laser at 365 nm wavelength. Pulsed laser beams or continuous laser beams may be used. The excitation beam passes through confocal optics and a microscope objective, and is focused onto the flow path and/or the flow-through cell. The Raman emission light from the labeled nanoparticles is collected by the microscope objective and the confocal optics and is coupled to a monochromator for spectral dissociation. The confocal optics includes a combination of dichroic filters, barrier filters, confocal pinholes, lenses, and mirrors for reducing the background signal. Standard full field optics can be used as well as confocal optics. The Raman emission signal is detected by a Raman detector, which includes an avalanche photodiode interfaced with a computer for counting and digitization of the signal.

Another example of a Raman detection unit is disclosed in U.S. Pat. No. 5,306,403, including a Spex Model 1403 double-grating spectrophotometer with a gallium-arsenide photomultiplier tube (RCA Model C31034 or Burle Industries Model C3103402) operated in the single-photon counting mode. The excitation source includes a 514.5 nm line argon-ion laser from SpectraPhysics, Model 166, and a 647.1 nm line of a krypton-ion laser (Innova 70, Coherent).

Alternate excitation sources include a nitrogen laser (Laser Science Inc.) at 337 nm and a helium-cadmium laser (Liconox) at 325 nm (U.S. Pat. No. 6,174,677), a light emitting diode, an Nd:YLF laser, and/or various ions lasers and/or dye lasers. The excitation beam may be spectrally purified with a bandpass filter (Corion) and may be focused on the flow path and/or flow-through cell using a 6× objective lens (Newport, Model L6X). The objective lens may be used to both excite the Raman-active organic compounds of the COINs and to collect the Raman signal, by using a holographic beam splitter (Kaiser Optical Systems, Inc., Model HB 647-26N18) to produce a right-angle geometry for the excitation beam and the emitted Raman signal. A holographic notch filter (Kaiser Optical Systems, Inc.) may be used to reduce Rayleigh scattered radiation. Alternative Raman detectors include an ISA HR-320 spectrograph equipped with a red-enhanced intensified charge-coupled device (RE-ICCD) detection system (Princeton Instruments). Other types of detectors may be used, such as Fourier-transform spectrographs (based on Michaelson interferometers), charged injection devices, photodiode arrays, InGaAs detectors, electron-multiplied CCD, intensified CCD and/or phototransistor arrays.

Any suitable form or configuration of Raman spectroscopy or related techniques known in the art may be used for detection of the nanoparticles of the present invention, including but not limited to normal Raman scattering, resonance Raman scattering, surface enhanced Raman scattering, surface enhanced resonance Raman scattering, coherent anti-Stokes Raman spectroscopy (CARS), stimulated Raman scattering, inverse Raman spectroscopy, stimulated gain Raman spectroscopy, hyper-Raman scattering, molecular optical laser examiner (MOLE) or Raman microprobe or Raman microscopy or confocal Raman microspectrometry, three-dimensional or scanning Raman, Raman saturation spectroscopy, time resolved resonance Raman, Raman decoupling spectroscopy or UV-Raman microscopy.

EXAMPLE 1

Synthesis Considerations

Chemical reagents: Biological reagents including anti-IL-2 and anti-IL-8 antibodies were purchased from BD Biosciences Inc. The capture antibodies were monoclonal antibodies generated from mouse. Detection antibodies were polyclonal antibodies generated from mouse and conjugated with biotin. Aqueous salt solutions and buffers were purchased from Ambion, Inc. (Austin, Tex., USA), including 5 M NaCl, 10×PBS (1×PBS 137 mM NaCl, 2.7 mM KCl, 8 mM $Na_2HPO_4$, and 2 mM $KH_2PO_4$, pH 7.4). Unless otherwise indicated, all other chemicals were purchased, at highest available quality, from Sigma Aldrich Chemical Co. (St. Louis, Mo., USA). Deionized water used for experiments had a resistance of $18.2 \times 10^6$ Ohms-cm and was obtained with a water purification unit (Nanopure Infinity, Barnstad, USA).

Silver seed particle synthesis: Stock solutions (0.500 M) of silver nitrate ($AgNO_3$) and sodium citrate ($Na_3$Citrate) were filtered twice through 0.2 micron polyamide membrane filters (Schleicher and Schuell, N. H., USA) which were thoroughly rinsed before use. Sodium borohydrate solution (50 mM) was made fresh and used within 2 hours. Silver seed particles were prepared by rapid addition of 50 mL of Solution A (containing 8.00 mM $Na_3$Citrate, 0.60 mM sodium borohydrate, and 2.00 mM sodium hydroxide) into 50 mL of Solution B (containing 4.00 mM silver nitrate) under vigorous stirring. Addition of Solution B into Solution A led to a more polydispersed suspension. Silver seed suspensions were stored in the dark and used within one week. Before use, the suspension was analyzed by Photon Correlation Spectroscopy (PCS, Zetasizer 3000 HS or Nano-ZS, Malvern) to ensure the intensity-averaged diameter (z-average) was between 10-12 nm with a polydispersity index of <0.25.

Gold seed particle synthesis: A household microwave oven (1350 W, Panasonic) was used to prepare gold nanoparticles. Typically, 40 mL of an aqueous solution containing 0.500 mM $HAuCl_4$ and 2.0 mM sodium citrate in a glass bottle (100 mL) was heated to boiling in the microwave using the maximum power, followed by a lower power setting to keep the solution gently boiling for 5 min. 2.0 grams of PTFE boiling stones (6 mm, Saint-Gobain A1069103, through VWR) were added to the solution to promote gentle and efficient boiling. The resultant solutions had a rosy red color. Measurements by PCS showed that the gold solutions had a typical z-average of 13 nm with a polydispersity index of <0.04.

COIN Synthesis:

In general, Raman labels were pipetted into the COIN synthesis solution to yield final concentrations of the labels in synthesis solution of about 1 to about 50 μM. In some cases, acid or organic solvents were used to enhance label solubility. For example, 8-aza-adenine and N-benzoyladenine were pipetted into the COIN formation reaction as 1.00 mM solutions in 1 mM HCl, 2-mercapto-benzimidazole was added from a 1.0 mM solution in ethanol, and 4-amino-pyrazolo[3,4-d]pyrimidine and zeatin were added from a 0.25 mM solution in 1 mM $HNO_3$.

Reflux method: To prepare COIN particles with silver seeds, typically, 50 mL silver seed suspension (equivalent to 2.0 mM $Ag^+$) was heated to boiling in a reflux system before introducing Raman labels. Silver nitrate stock solution (0.50 M) was then added dropwise or in small aliquots (50-100 μL) to induce the growth and aggregation of silver seed particles. Up to a total of 2.5 mM silver nitrate could be added. The solution was kept boiling until the suspension became very turbid and dark brown in color. At this point, the temperature was lowered quickly by transferring the colloid solution into a glass bottle. The solution was then stored at room temperature. The optimum heating time depended on the nature of Raman labels and amounts of silver nitrate added. It was found helpful to verify that particles had reached a desired size range (80-100 nm on average) by PCS or UV-Vis spectroscopy before the heating was arrested. Normally, a dark brown color was an indication of cluster formation and associated Raman activity.

To prepare COIN particles with gold seeds, typically, gold seeds were first prepared from 0.25 mM $HAuCl_4$ in the presence of a Raman label (for example, 20 μM 8-aza-adenine). After heating the gold seed solution to boiling, silver nitrate and sodium citrate stock solutions (0.50 M) were added, separately, so that the final gold suspension contained 1.0 mM $AgNO_3$ and 1.0 mM sodium citrate. Silver chloride precipitate might form immediately after silver nitrate addition but disappeared soon with heating. After boiling, an orange-brown color developed and stabilized. An additional aliquot (50-100 μL) of silver nitrate and sodium citrate stock solutions (0.50 M each) was added to induce the development of a green color, which was the indication of cluster formation and was associated with Raman activity.

Note that the two procedures produced COINs with different colors, primarily due to differences in the size of primary particles before cluster formation.

Oven method: COINs could also be prepared conveniently by using a convection oven. Silver seed suspension was mixed with sodium citrate and silver nitrate solutions in a 20 mL glass vial. The final volume of the mixture was typically 10 mL, which contained silver particles (equivalent to 0.5 mM $Ag^+$), 1.0 mM silver nitrate and 2.0 mM sodium citrate (including the portion from the seed suspension). The glass vials were incubated in the oven, set at 95° C., for 60 min. before being stored at room temperature. A range of label concentrations could be tested at the same time. Batches showing brownish color with turbidity were tested for Raman activity and colloidal stability. Batches with significant sedimentation (which occurred when the label concentrations were too high) were discarded. Occasionally, batches that did not show sufficient turbidity could be kept at room temperature for an extended period of time (up to 3 days) to allow cluster formation. In many cases, suspensions became more turbid over time due to aggregation, and strong Raman activity developed within 24 hours. A stabilizing agent, such as bovine serum albumin (BSA), could be used to stop the aggregation and stabilize the COIN suspension.

A similar approach was used to prepare COINs with gold cores. Briefly, 3 mL of gold suspensions (0.50 mM $Au^{+++}$) prepared in the presence of Raman labels was mixed with 7 mL of silver citrate solution (containing 5.0 mM silver nitrate and 5.0 mM sodium citrate before mixing) in a 20 mL glass vial. The vial was placed in a convection oven and heated to 95° C. for 1 hour. Different concentrations of labeled gold seeds could be used simultaneously in order to produce batches with sufficient Raman activities.

Cold Method: 100 mL of silver particles (1 mM silver atoms) were mixed with 1 mL of Raman label solution (typically 1 mM). Then, 5 to 10 mL of 0.5 M LiCl solution was added to induce silver aggregation. As soon as the suspension became visibly darker (due to aggregation), 0.5% BSA was added to inhibit the aggregation process. Afterwards, the suspension was centrifuged at 4500 g for 15 minutes. After removing the supernatant (mostly single particles), the pellet was resuspended in 1 mM sodium citrate solution. The washing procedure was repeated for a total of three times. After the last washing, the resuspended pellets were filtered through 0.2 μM membrane filter to remove large aggregates. The filtrate was collected as COIN suspension. The concentrations of COINs were adjusted to 1.0 or 1.5 mM with 1 mM sodium citrate by comparing the absorbance at 400 nm with 1 mM silver colloids for SERS.

It should be noted that a COIN sample can be heterogeneous in terms of size and Raman activity. We typically used centrifugation (200-2,000×g for 5-10 min.) or filtration (300 kDa, 1000 kDa, or 0.2 micron filters, Pall Life Sciences through VWR) to enrich for particles in the range of 50-100 nm. It is recommended to coat the COIN particles with a protection agent (for example, BSA, antibody) before enrichment. Some lots of COINs that we prepared (with no further treatment after synthesis) were stable for more than 3 months at room temperature without noticeable changes in physical and chemical properties.

Figure 10A:
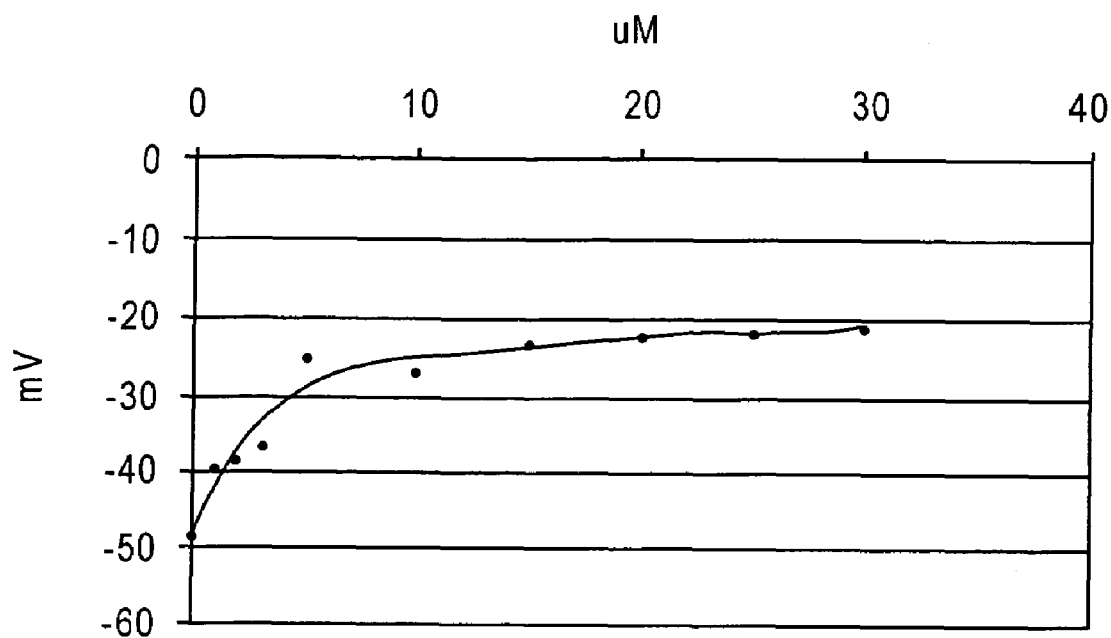
FIGS. 10A and B show, respectively, the zeta potential measurements of silver particles and the evolution of aggregate size (z-average) in the presence of 20 µM 8-azaadenine.
Figure 10B:
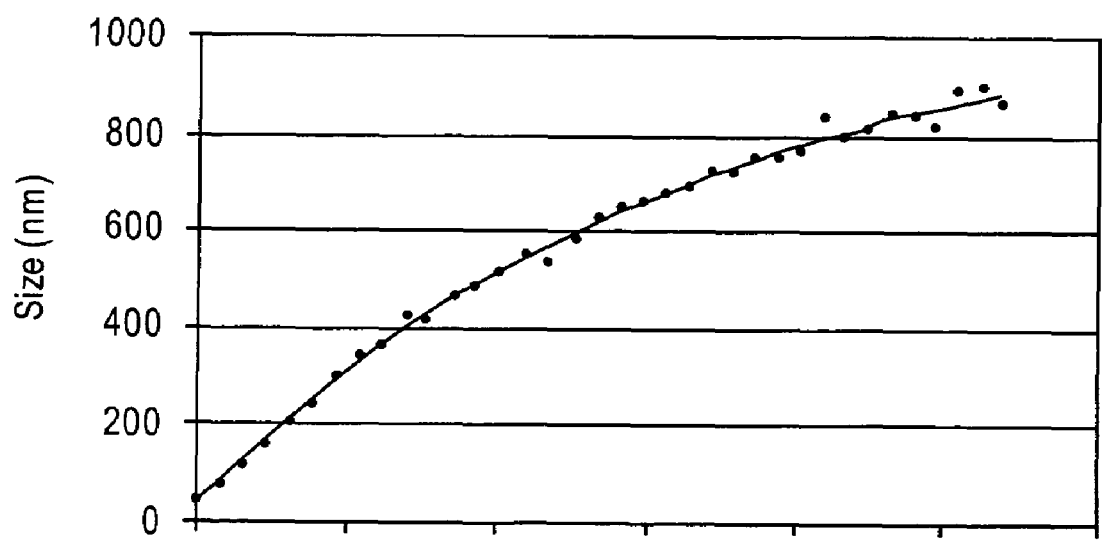

Particle size measurement: The sizes of silver and gold seed particles as well as COINs were determined by using Photon Correlation Spectroscopy (PCS, Zetasizer3 3000 HS or Nano-ZS, Malvern). All measurements were conducted at 25° C. using a He—Ne laser at 633 nm. Samples were diluted with DI water when necessary. Some of the COIN samples (with a total silver concentration of 1.5 mM) were diluted ten times with 1 mM sodium citrate before measurement. FIGS. 10A and B show, respectively, the zeta potential measurements of silver particles of initial z-average size of 47 nm (0.10 M) with a suspending medium of 1.00 mM sodium citrate and the evolution of aggregate size (z-average) in the presence of 20 μM 8-aza-adenine.

Raman spectral analysis: for all SERS and COIN assays in solution, a Raman microscope (Renishaw, UK) equipped with a 514 nm Argon ion laser (25 mW) was used. Typically, a drop (50-200 μL) of a sample was placed on an aluminum surface. The laser beam was focused on the top surface of the sample meniscus and photons were collected for about 10-20 seconds. The Raman system normally generated about 600 counts from methanol at 1040 $cm^{-1}$ for a 10 second collection time. For Raman spectroscopy detection of an analyte immobilized on a surface, Raman spectra were recorded using a Raman microscope built in-house. This Raman microscope consisted of a water cooled Argon ion laser operating in continuous-wave mode, a dichroic reflector, a holographic notch filter, a Czerny-Turner spectrometer, and a liquid nitrogen cooled CCD (charge-coupled device) camera. The spectroscopy components were coupled with a microscope so that the microscope objective focused the laser beam onto a sample, and collected the back-scattered Raman emission. The laser power at the sample was about 60 mW. All Raman spectra were collected with 514 nm excitation wavelength.

Antibody Coating

A 500 μL solution containing 2 ng of a biotinylated anti-human antibody (anti-IL-2 or anti-IL-8) in 1 mM sodium citrate (pH 9) was mixed with 500 μL of a COIN solution (made with 8-aza-adenine or N-benzoyl-adenine); the resulting solution was incubated at room temperature for 1 hour, followed by adding 100 μL of PEG-400 (polyethyleneglycol-400). The solution was incubated at room temperature for another 30 min., then 200 μL of 1% Tween™-20 was added to the solution. The solution was centrifuged at 2000×g for 10 min. After removing the supernatant, the pellet was resuspended in 1 mL solution (BSAT) containing 0.5% BSA, 0.1% Tween-20 and 1 mM sodium citrate. The solution was then centrifuged at 1000×g for 10 min. The BSAT washing procedure was repeated for a total of 3 times. The final pellet was resuspended in 700 µL of diluting solution (0.5% BSA, 1×PBS, 0.05% Tween™-20). The Raman activity of the COINs was measured and adjusted to a specific activity of about 500 photon counts per µl per 10 seconds using a Raman spectroscope that generated about 600 counts from methanol at 1040 cm$^{-1}$ for 10 second collection time.

Confirmation of antibody-COIN conjugation: To obtain a standard curve, sandwich immunoassay experiments were performed according to manufacture's instruction (BD Biosciences), using immobilized capture antibody, fixed analyte concentration (5 ng/mL IL-2 protein) and a serially diluted detection antibody (0, 0.01, 0.1, 1, and 10 µg/mL). After detection antibody binding, streptavidin-HRP (Horse Radish Peroxidase) was then reacted with the biotinylated detection antibodies and TMB (tetramethyl benzidine) substrate was applied followed by UV absorption measurement. A standard curve was generated by plotting absorption values against antibody concentrations.

EXAMPLE 2

Synthesis of COINs Coated with BSA

Coating Particles with BSA: COIN particles were coated with an adsorption layer of BSA by adding 0.2% BSA to the COIN synthesis solution when the desired COIN size was reached. The addition of BSA inhibited further aggregation.

Crosslinking the BSA Coating: The BSA adsorption layer was crosslinked with glutaraldehyde followed by reduction with NaBH$_4$. Crosslinking was accomplished by transferring 12 mL of BSA coated COINs (having a total silver concentration of about 1.5 mM) into a 15 mL centrifuge tube and adding 0.36 g of 70% glutaraldehyde and 213 µL of 1 mM sodium citrate. The solution was mixed well and allowed to sit at room temperature for about 10 min. before it was placed in a refrigerator at 4° C. The solution remained at 4° C. for at least 4 hours and then 275 µL of freshly prepared NaBH$_4$ (1 M) was added. The solution was mixed and left at room temperature for 30 min. The solution was then centrifuged at 5000 rpm for 60 min. The supernatant was removed with a pipet leaving about 1.2 mL of liquid and the pellet in the centrifuge tube. The COINs were resuspended by adding 0.8 mL of 1 mM sodium citrate to yield a final volume of 2.0 mL.

FPLC Purification of Encapsulated COINS: The coated COINs were purified by FPLC (fast protein liquid chromatography) on a crosslinked agarose size-exclusion column. The concentrated COIN reaction mixture suspension (2.0 mL) was purified with a Superose 6 FPLC column on an AKTA Purifier. The COIN mixture was injected in 0.5 ml batches and an isocratic flow of 1 mM sodium citrate at 1 ml/min was applied to the column. Absorbance at 215 nm, 280 nm, and 500 nm was monitored for peak collection. The encapsulated COINs eluted at about 7-9 min., while the BSA/crosslinked BSA fraction eluted at about 9-11 min. Glutaraldehyde, sodium borohydride, and Raman labels eluted after about 20 min. Fractions from multiple FPLC runs were combined.

Figure 11A:
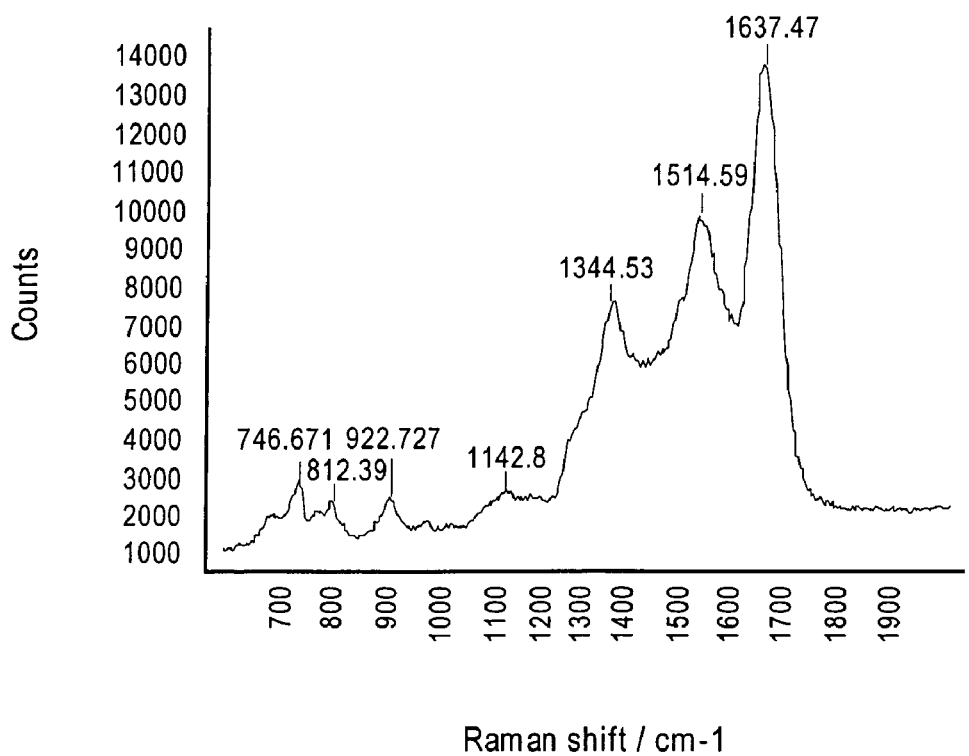
FIGS. 11A and B show Raman spectra from encapsulated COINs.
Figure 11B:
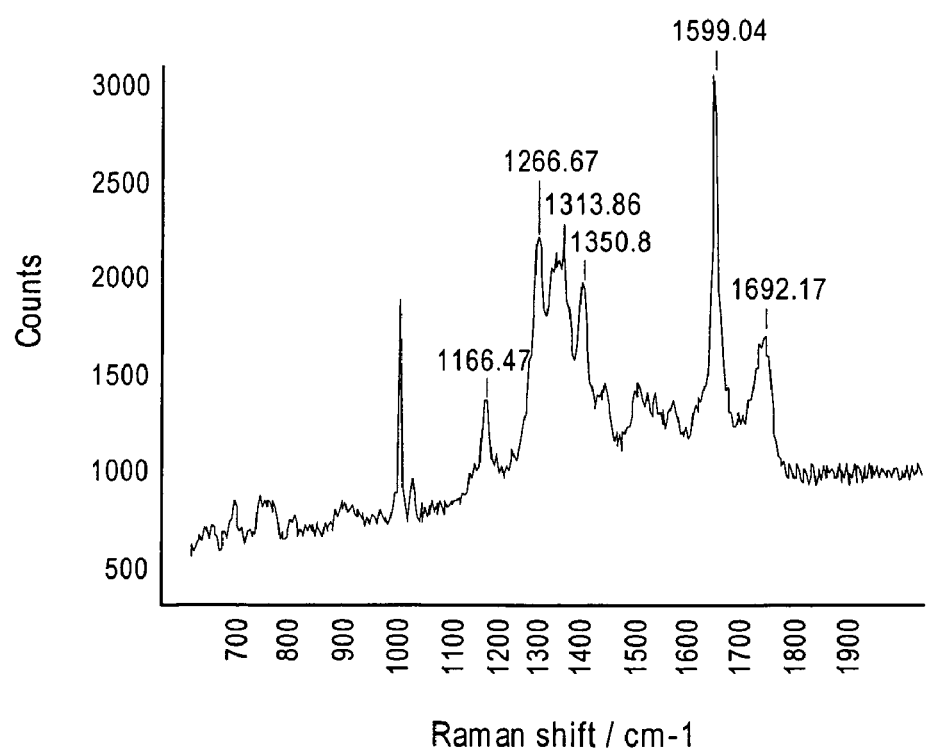

FIGS. 11A and B show Raman spectra obtained from AIC and BZA encapsulated COINs, respectively. COINs were encapsulated with crosslinked BSA as described in this Example. Raman spectra were obtained from an aqueous solution of COINs having a concentration of about 0.1 mM (total silver) on a Raman microscope (Renishaw, UK) and were normalized using methanol's Raman signal.

Thermostabilization Test of Coated COINs: The thermal stability of crosslinked BSA-coated COINs was measured by taking 20 mL of the AAD COIN solution obtained from the FPLC purification and diluting it 10 times with 1 mM sodium citrate. The solution was then evenly split between two PCR tubes. One of the tubes was heated to 70° C. for 5 min., followed by addition of 5 µL of 0.5M LiCl to yield a final concentration of 25 mM. The other tube was used as a control and kept at room temperature. Raman signals from both samples were measured and signal intensities from the main peaks were compared. FIGS. 12A and B show Raman spectra that were obtained as a result of the thermostabilization tests. FIG. 12A shows the Raman spectrum obtained from a COIN having a BSA coating before heating and LiCl addition. FIG. 12B shows the spectrum of the coated AAD COINs after heating and LiCl addition. FIG. 12C shows a plot comparing signal strength (at 1346 cm$^{-1}$) as the concentration of LiCl was increased. The top data is from the encapsulated (crosslinked BSA) COINs and the bottom data is from the BSA-coated COINs. As can be seen, crosslinking BSA can increase COIN stability. Raman spectra were obtained from an aqueous solution of COINs having a concentration of about 0.1 mM (total silver) on a Raman microscope (Renishaw, UK) equipped with a 514 nm Argon ion laser and were normalized using methanol's Raman signal.

Figure 13:
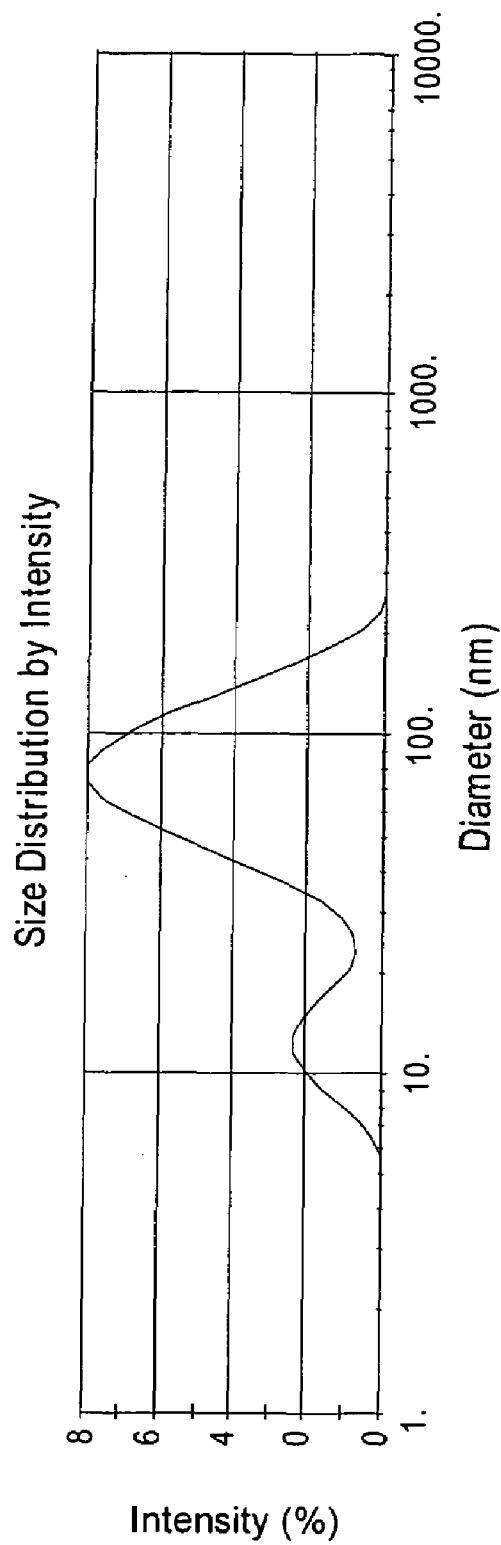
FIG. 13 shows an intensity weighted size distribution of encapsulated AMA (9-amino-acridine) COINs.

Size Stability Test: The colloidal stability of encapsulated COINs (COINs coated with crosslinked BSA) was determined by measuring the size distribution of a sample over a period of 10 to 12 days. FIG. 13 shows the size distribution for a sample of AMA COINs measured on by Photon Correlation Spectroscopy (PCS Zetasizer3 3000 HS or Nano-ZS, Malvern). Typically, COINs show a bimodal size distribution as can be seen in FIG. 13. In this case, the population of smaller sized particles is primarily silver particles (as confirmed by TEM) and the population of larger sized particles (about 60 to about 120 nm) are COIN particles. The z-average diameter, the polydispersity, and the average COIN size represented by the main peak are given in Table 2.

TABLE 2

Size stability of encapsulated COINs having labels incorporated as indicated

| | Day 1 | | | Day 11 | | | % Change | | |
|---|---|---|---|---|---|---|---|---|---|
| Label | Z-ave/nm | PDI | Main Peak | Z-ave/nm | PDI | Main Peak | Z-ave/nm | PDI | Main Peak |
| AAD | 48.4 | 0.50 | 94.8 | 44.7 | 0.46 | 82.9 | −8.0 | −8.8 | −13.5 |
| AIC | 32.6 | 0.53 | 72.7 | 33.3 | 0.54 | 78.8 | 1.9 | 1.7 | 8.0 |
| AMA | 41.4 | 0.51 | 83.2 | 40.8 | 0.50 | 81.1 | −1.6 | −0.6 | −2.5 |

TABLE 2-continued

Size stability of encapsulated COINs having labels incorporated as indicated

| | Day 1 | | | Day 11 | | | % Change | | |
|---|---|---|---|---|---|---|---|---|---|
| Label | Z-ave/nm | PDI | Main Peak | Z-ave/nm | PDI | Main Peak | Z-ave/nm | PDI | Main Peak |
| APP | 42.1 | 0.52 | 83.0 | 46.3 | 0.49 | 90.8 | 9.7 | −5.7 | 8.9 |
| BZA | 55.8 | 0.27 | 77.6 | 62.9 | 0.40 | 87.9 | 11.9 | 36.9 | 12.5 |
| BRB | 49.4 | 0.31 | 75.6 | 49.1 | 0.31 | 74.4 | −0.6 | −1.6 | −1.6 |
| DAH | 67.8 | 0.25 | 96.6 | 66.9 | 0.27 | 95.0 | −1.3 | 6.2 | −1.6 |
| DII | 78.0 | 0.28 | 112.6 | 79.5 | 0.29 | 118.0 | 1.9 | 2.1 | 4.7 |
| EBR | 80.3 | 0.28 | 118.7 | 81.3 | 0.27 | 116.9 | 1.3 | −3.3 | −1.5 |
| FAD | 44.4 | 0.44 | 84.5 | 43.7 | 0.42 | 77.8 | −1.5 | −2.8 | −8.3 |
| MBL | 39.0 | 0.33 | 61.6 | 39.3 | 0.33 | 63.6 | 1.0 | 0.6 | 3.2 |
| THN | 44.2 | 0.51 | 101.1 | 41.6 | 0.54 | 83.9 | −6.2 | 5.7 | −18.6 |
| ZEN | 41.4 | 0.41 | 73.1 | 40.4 | 0.45 | 72.5 | −2.5 | 7.4 | −0.7 |
| AND | 28.5 | 0.47 | 62.6 | 28.8 | 0.48 | 63.3 | 0.9 | 2.1 | 1.1 |
| CRV | 61.9 | 0.39 | 94.8 | 68.6 | 0.29 | 103.3 | 10.2 | −27.8 | 8.6 |
| R6G | 47.9 | 0.43 | 84.1 | 50.3 | 0.43 | 86.3 | 4.8 | −0.7 | 2.5 |

As can be seen from Table 2, the changes in average size (z-average) are almost all less than 15% over a period of 11 days. However, in the case of THN COINs, a decrease of over 15% was seen in the main peak position. It is believed that this can be attributed to the uncertainty present for size measurements of samples having large size polydispersities.

Figure 14:
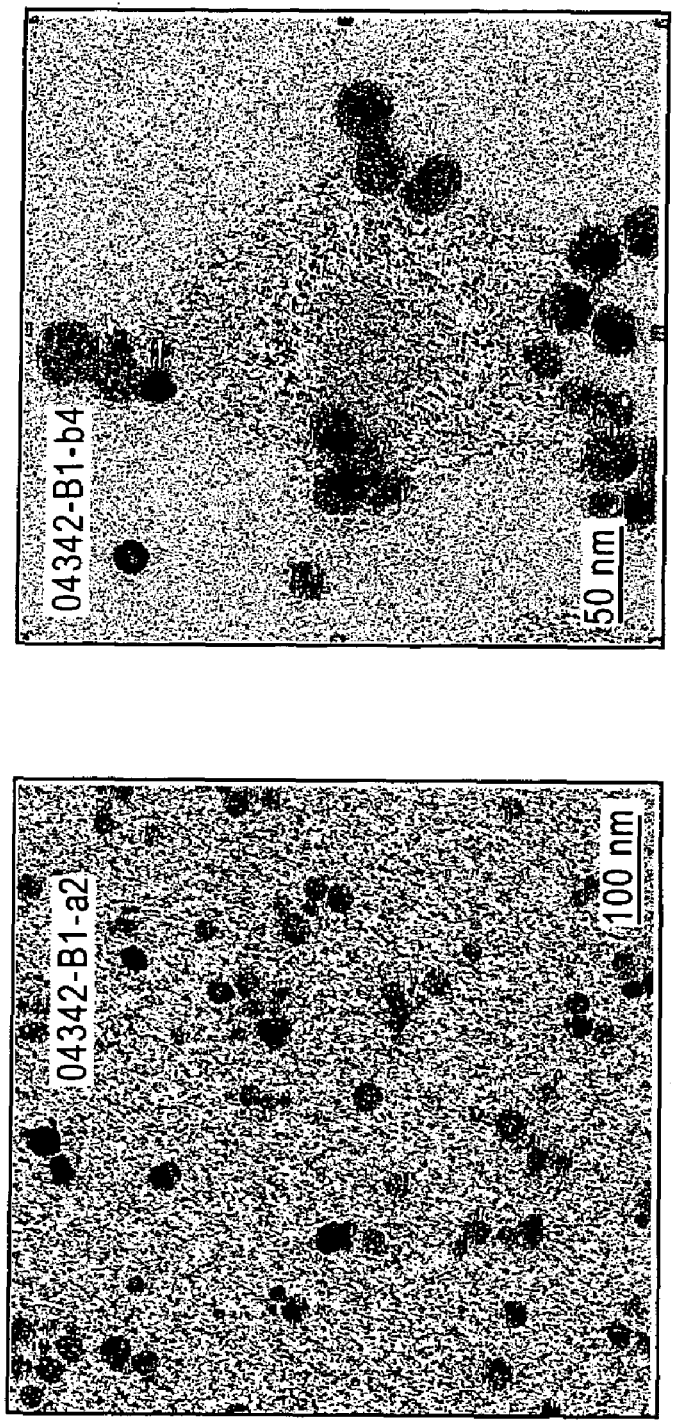
FIG. 14 shows TEM images from encapsulated AMA (9-amino-acridine) COINs.
Figure 15A:
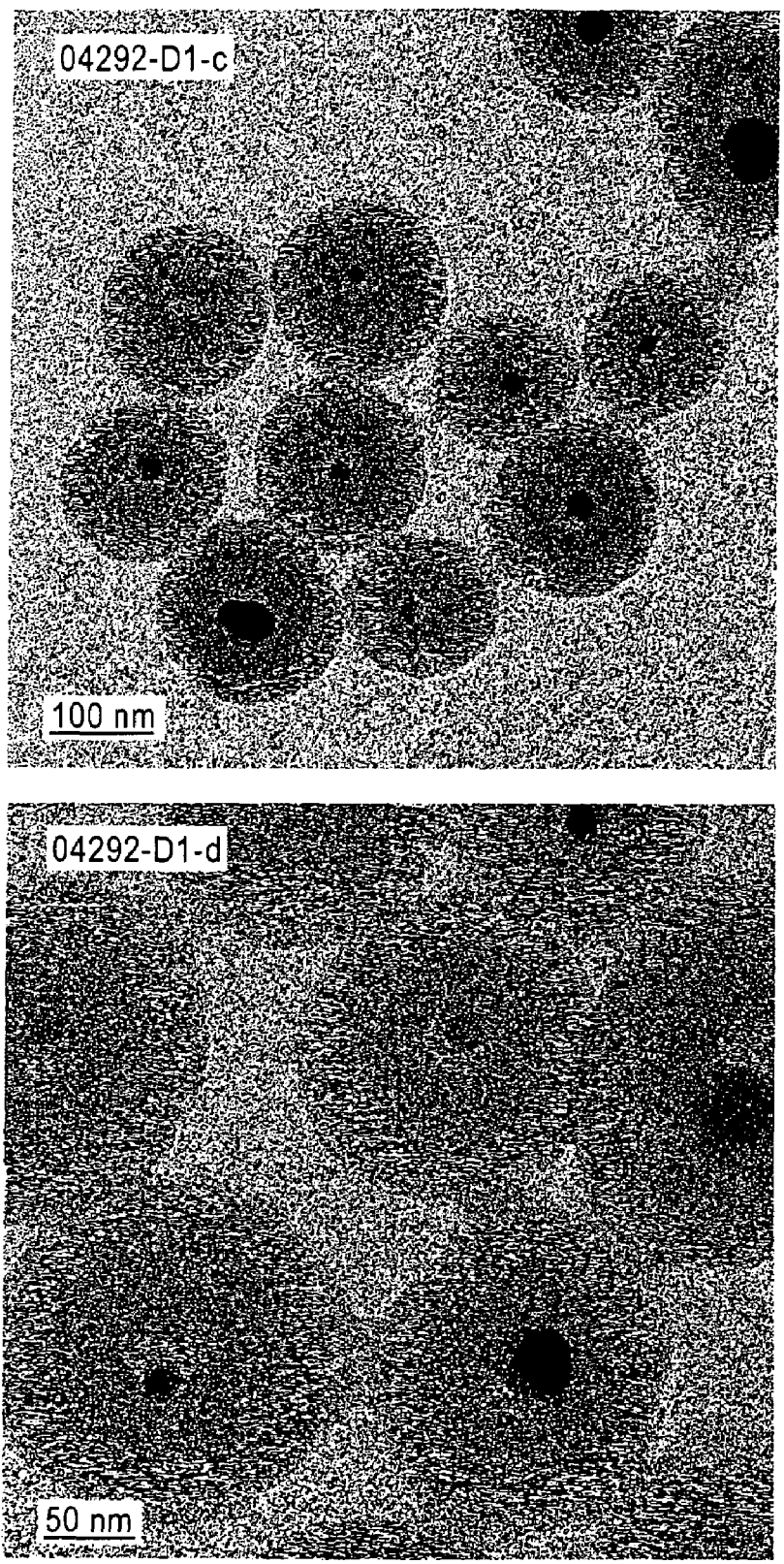
FIGS. 15A and B contain TEM images of silica coated silver particles and silica coated gold particles, respectively.
Figure 15B:
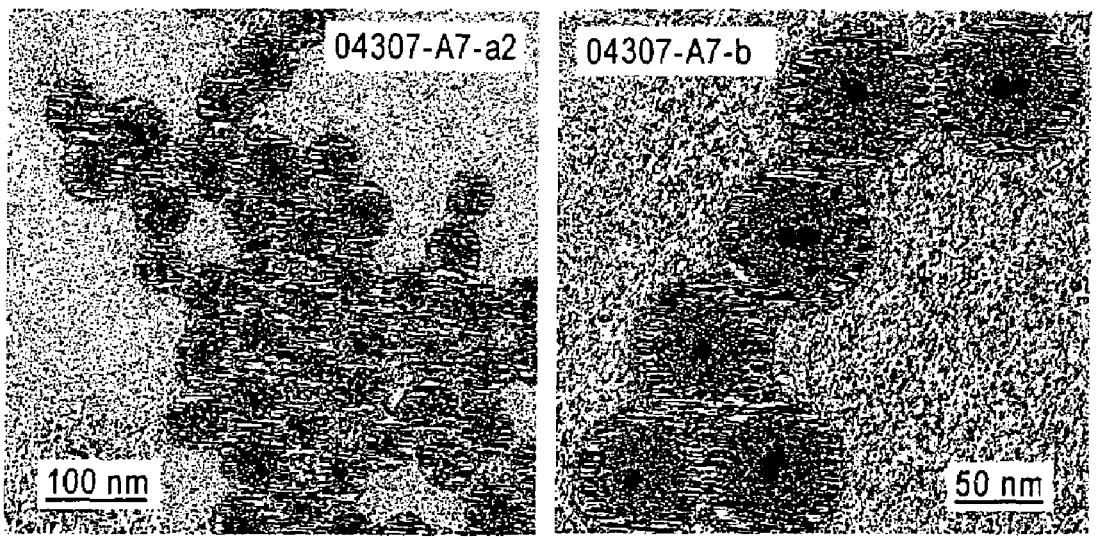
Figure 16:
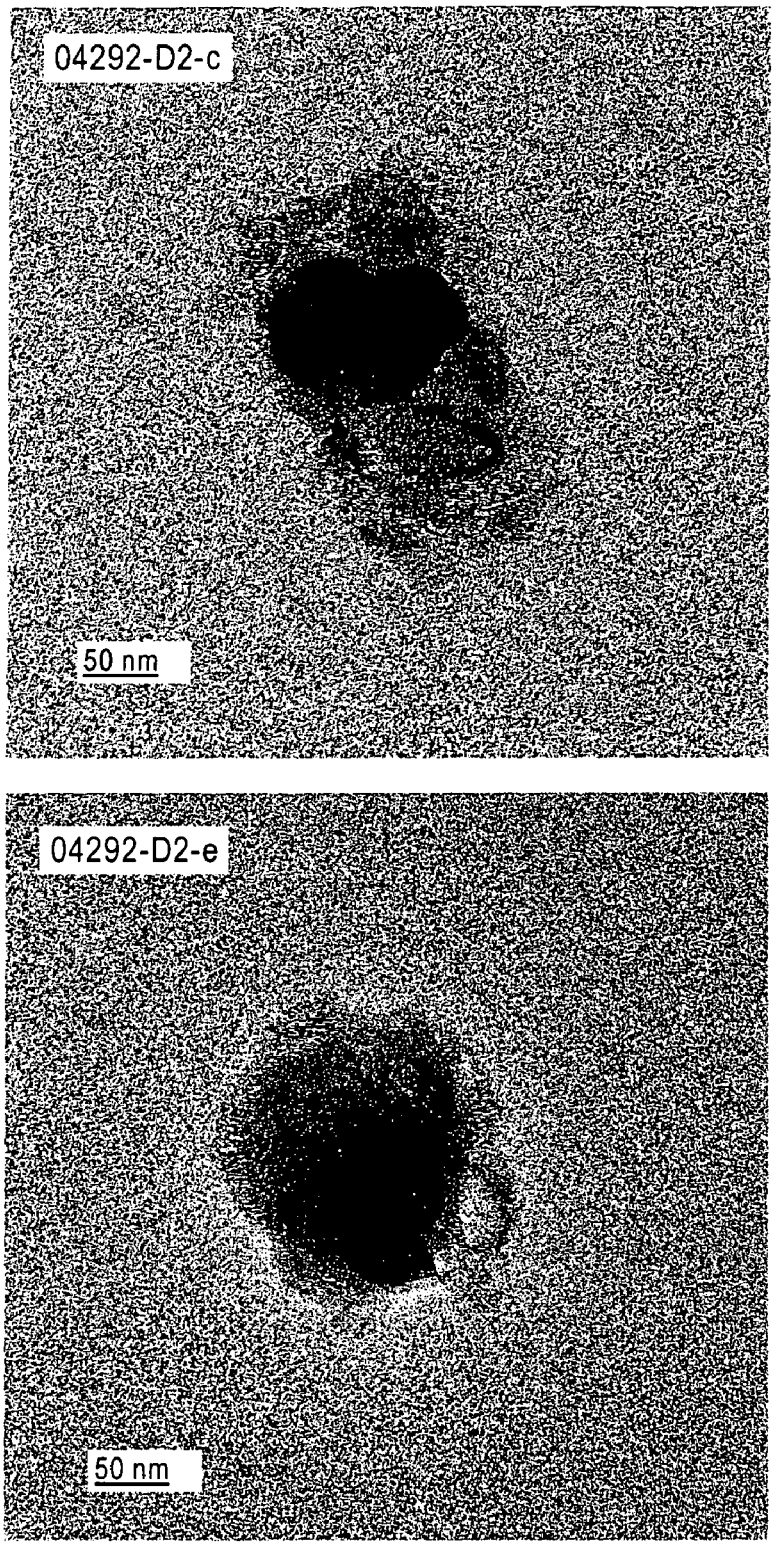
FIG. 16 contains TEM images of hematite ($\alpha$-$Fe_2O_3$) coated silver particles.

TEM of Encapsulated COINs: Encapsulated COINs were examined by TEM. The samples were prepared as follows: Carbon coated copper grids (200 mesh) were pretreated with a cationic polymer. 10 µL of 0.1% poly-L-lysine was added to a plastic petridish (a hydrophobic surface). The copper grid was placed on top of the drop. The polymer was allowed to absorb on the copper grid for 10 min. The grid was then washed by allowing it to touch a drop of deionized water (100 µL on a plastic surface) twice. The excess solution was blown away in a stream of nitrogen. The grid was allowed to dry for 15 min. The treated grid was then placed on a plastic surface and 5 µL of a COIN suspension (about 6 µM in total silver concentration) was placed on the grid. The colloid particles were allowed to absorb onto the grid for 10 min. The grid was then dried with blowing nitrogen. FIG. 14 shows TEM images from encapsulated AMA COINs. As can be seen, these COIN suspensions contain single particles and clusters of various sizes. The presence of small single particles has been confirmed by PCS measurements. It is believed that the irregular shape and size variation in COINs are due to the aggregation process during COIN synthesis.

Antibody Conjugation: To attach an antibody probe to the encapsulated COINs, 500 µL of the encapsulated COIN solution was mixed with ⅕ volume of 10 mM EDC in water (EDC: 1.92 mg, water: 1 mL) to yield a final EDC concentration of 2 mM. The COIN-EDC reaction was allowed to proceed at room temperature for 15 min. Then, 500 µL of water was added and the solution was centrifuged at 5000 g for 10 min. The supernatant was removed and the residue was re-suspended in 1 mL of water and 50 µL of 1% Tween-20. The solution was centrifuged again at 5000 g for 10 min. and the supernatant was removed. 150 µL of water and 10 µl of 500 µg/mL detection antibody (to a final conc. about 0.2 µM) was added and the conjugation was allowed to proceed at room temperature for 30 min. with shaking every 10 min. 20 µL of PEG-400 was added to the reaction mixture. After 10 min., 500 µL of COIN wash solution (1 mM citrate, 0.5% BSA, 0.05% Tween-20) was added. After another 10 min., the mixture was centrifuged at 2000 g for 10 min., the supernatant was removed, and the pellet was washed 2 more times with COIN wash solution. The final COIN-ab product was re-suspended in 50 µL of 1 mM citrate and the Raman signal was measured. The product was stored at 4° C. until binding activity and protein assay were performed (usually within a week).

Confirmation of Antibody-COIN Conjugation

Surface Preparation: 400 µL DI water, 200 µL 1×PBS, and 12 µL of 500 µg/mL of mouse Anti-Human IL2 antibody were mixed. The resulting solution was pipetted in 100 µL increments into 6 wells of a 96-well plate and incubated for 2 hr at 37° C. or overnight at 4° C. To block the surface, the antibody solution was removed and 200 µL of 1% BSA solution was added to each well and incubated at 37° C. for 1 hour. The wells were washed 4 times with 200 µL of wash solution (1×PBS, 0.05% Tween-20) after blocking. Then, 10 ng/mL of IL2 protein solution in diluting solution (1×PBS, 0.05% Tween-20, 0.5% BSA) was prepared and 100 µL was added to each of the 6 antibody wells and incubated at 37° C. for 30 min. The wells were then washed 4 times with 200 µL of wash solution (0.05% Tween-20, 1×PBS).

Detection Antibody Binding: The COIN-Bt-A-IL2 conjugate (COIN conjugated with a biotinylated anti-IL2 antibody) solution and Bt-A-IL2 solution were introduced into the wells according to the Table 3. The COIN-ab solution was faintly yellow gave a Raman signal of about 1000-5000 counts. The wells were incubated at 37° C. for half an hour, the conjugate solution was removed, and the wells were washed with 200 µL of wash solution 4 times.

TABLE 3

| Well | COIN(THN)-Bt-A-IL2 | Bt-A-IL2 | diluting sol. |
|---|---|---|---|
| 1 | 50 µL | 0 | 50 µL |
| 2 | 5 µL | 0 | 95 µL |
| 3 | 0 | 0 | 0 |
| 4 | 0 | 10 µL | 90 µL |
| 5 | 0 | 1 µL | 99 µL |
| 6 | 0 | 0.1 µL | 99.9 µL |

Substrate Visualization: A streptavidin-horseradish peroxidase conjugate (Catalog # DY998, R&D Systems) was diluted to its pre-titered optimal concentration (1:200) in diluting solution. 100 µl was added to each well. The plate was sealed and incubated at 37° C. for 20 min. The wells were washed at least 5 times with 0.05% Tween-20 in 1×PBS. A substrate solution of 1:1 mixture of Color Reagent A ($H_2O_2$) and Color Reagent B (Tetramethyl Benzidine (R&D systems, Catalog # DY999)) was prepared and used within 20 min. of preparation. 100 µl of substrate solution was added to each well and incubated at room temperature for 20-30 min. for color development. Direct light was avoided. Then, 50 µL of stop solution (1 mM $H_2SO_4$) was added to each well and the optical density (OD) at 450 nm was read for each well with a UV-Vis spectrophotometer. The COIN-Bt-A-IL2 showed antigen-binding activities that were similar to free Bt-A-IL2 detection antibody.

EXAMPLE 3

Synthesis of Silver and Gold Particles Coated with Silica

Silver COINs are coated with silica by adding 100 μL TEOS to a stirred solution of 75 mL 100% ethanol and 20 mL of a dilute COIN suspension created by adding about 1 to about 10 mL of a 1 mM COIN solution to deionized water. Then, 5 mL of a 28% $NH_3$ solution is added and the solution is maintained at room temperature with gentle stirring for 19 hours. The final molar composition of the coating solution is 4.6 mM TEOS and 0.82 M $NH_3$. At the end of 19 hours, the solution is diluted 4× with deionized water and centrifuged at 5000 rpm for 15 min. to remove the organic solvent. The suspending solution is replaced with 1 mM sodium citrate.

FIG. 11A provides TEM images of silica-coated silver seed particles that were according to the preceding procedure. The thickness of the resulting coating was about 50 nm. The thickness can be reduced by (a) adding more silver particles, (b) reducing the TEOS concentration, or (c) decreasing the coating time.

The above coating procedure was used to coat gold particles as well. FIG. 11B provides TEM images of gold particles coated with Silica. Our results indicate that pretreatment with silane-based coupling reagents is not necessary to promote the formation of a silica coating.

EXAMPLE 4

Synthesis of COINs Coated with Hematite

A 100 μL suspension of silver COINs is mixed with 0.9 mL of hematite solution (1 mM $Fe_2O_3$, 8 nm particles). The resulting mixture is centrifuged at 10,000 rpm for 15 min. 0.95 mL of supernatant is withdrawn and 1.00 mL of 1 mM HCl is added to resuspend the pellet. The resulting suspension is then centrifuged at 10,000 rpm again for 15 min and 0.95 mL of supernatant is withdrawn. 1.00 mL of 1 mM HCl is added to resuspend the pellet. The resulting COINs are coated with a layer of hematite particles.

FIG. 12 provides a TEM image of silver seed particles that were coated with hematite according to the preceding procedure. As can be seen from the image, the small positively charged hematite particles coated the silver particles. It is believed that the hematite particles coated the silver particles due to coulombic interaction.

What is claimed:

1. A nanocluster of metal particles having a unique Raman signature, wherein the unique Raman signature is produced by at least one Raman active organic compound, and wherein at least one Raman active organic compound is embedded within the nanocluster and at least one Raman active organic compound is located on a surface of the nanocluster, also including a protein adsorption layer on the surface of the nanocluster comprising a non-enzymatic globular or fibrous protein.

2. The nanocluster of claim 1 wherein the metal particles are comprised of a metal selected from group consisting of silver, gold, copper, palladium, platinum, and aluminum.

3. The nanocluster of claim 1 wherein the metal particles are comprised of silver or gold.

4. The nanocluster of claim 1 wherein the nanocluster has an average diameter of about 20 nm to about 200 nm.

5. The nanocluster of claim 1 wherein the nanocluster has an average diameter of about 40 to about 200 nm.

6. The nanocluster of claim 2 or 5 wherein the protein layer is comprised of a protein selected from the group consisting of avidin, streptavidin, bovine serum albumen, transferrin, insulin, soybean protein, casine, gelatine, and mixtures thereof.

7. The nanocluster of claim 2 or 5 wherein the protein layer is crosslinked with glutaraldehyde and is comprised of a protein selected from the group consisting of avidin, streptavidin, bovine serum albumen, insulin, soybean protein, casine, gelatine, and mixtures thereof.

8. The nanocluster of claim 1 wherein the nanocluster has an average diameter of about 50 nm to 150 nm.

9. The nanocluster of claim 1 wherein the nanocluster having a protein coating further comprises a probe selected from the group consisting of antibodies, antigens, polynucleotides, oligonucleotides, receptors, cofactors, carbohydrates, and ligands.

10. The nanocluster of claim 1 wherein the metal particles are comprised of silver, the nanocluster is coated with a layer of gold, and the protein layer is adsorbed thereon.

11. The nanocluster of claim 1 wherein the nanocluster contains two different organic compounds capable of being detected by Raman spectroscopy incorporated therein.

12. The nanocluster of claim 1 wherein the nanocluster contains three different organic compounds capable of being detected by Raman spectroscopy incorporated therein.

13. A method for making a Raman active nanocluster of claim 1 comprising:

providing a solution comprising suspended metal nanoparticles and a Raman active organic compound;

heating the solution comprising metal nanoparticles and the Raman-active organic compound in the presence of a metal cation under conditions that allow the formation of nanoclusters comprising the metal nanoparticles and the Raman active organic compound; and adding a non-enzymatic globular protein to the solution comprising nanoclusters under conditions that allow the non-enzymatic globular protein to adsorb to surfaces of the nanoclusters.

14. The method of claim 13 wherein two or more different Raman active organic compounds are added to the solution comprising suspended metal nanoparticles.

15. The method of claim 13 wherein the metal particles are comprised of silver, gold, or combinations thereof.

16. The method of claim 13 wherein the protein is selected from the group consisting of avidin, streptavidin, bovine serum albumen, transferrin, insulin, soybean protein, casine, gelatine, and mixtures thereof.

17. The method of claim 13 further comprising coupling a probe molecule to the surfaces of the nanoclusters wherein the probe molecule is selected from the group consisting of antibodies, antigens, polynucleotides, oligonucleotides, receptors, cofactors, carbohydrates, and ligands.

18. A nanocluster of metal particles having a unique Raman signature, wherein the nanocluster is comprised of three to five metal nanoparticles, wherein the unique Raman signature is produced by at least one Raman active organic compound incorporated within the nanocluster, wherein the nanocluster has a surface, and wherein the surface of the nanocluster is at least partially coated with a protein adsorption layer, and wherein the protein adsorption layer composes a non-enzymatic globular or fibrous protein.

19. The nanocluster of claim 18 wherein the metal particles are comprised of a metal selected from group consisting of silver, gold, copper, palladium, platinum, and aluminum.

20. The nanocluster of claim 18 wherein the metal particles are comprised of silver, gold, or combinations thereof.

21. The nanocluster of claim 18 wherein the protein is selected from the group consisting of avidin, streptavidin, bovine serum albumen, transferrin, insulin, soybean protein, casine, gelatine, and mixtures thereof.

22. The nanocluster of claim 18 wherein the protein adsorption layer comprises crosslinked protein.

23. The nanocluster of claim 18 further comprising a probe selected from the group consisting of antibodies, antigens, polynucleotides, oligonucleotides, receptors, cofactors, carbohydrates, and ligands.

* * * * *